(12) United States Patent
Huber et al.

(10) Patent No.: US 10,497,465 B2
(45) Date of Patent: Dec. 3, 2019

(54) METHOD FOR CHARACTERIZING A SAMPLE BY DATA ANALYSIS

(75) Inventors: Fritz Huber, Regensburg (DE); Renate Kirchhoefer, Regensburg (DE); Volker Pfahlert, Kandern (DE)

(73) Assignee: numares AG, Regensburg (DE)

( * ) Notice: Subject to any disclaimer, the term of this patent is extended or adjusted under 35 U.S.C. 154(b) by 803 days.

(21) Appl. No.: 13/878,094

(22) PCT Filed: Oct. 5, 2011

(86) PCT No.: PCT/EP2011/067383
§ 371 (c)(1),
(2), (4) Date: Apr. 5, 2013

(87) PCT Pub. No.: WO2012/045773
PCT Pub. Date: Apr. 12, 2012

(65) Prior Publication Data
US 2013/0289887 A1 Oct. 31, 2013

Related U.S. Application Data

(60) Provisional application No. 61/391,317, filed on Oct. 8, 2010.

(30) Foreign Application Priority Data

Oct. 6, 2010 (DE) ........................ 10 2010 038 014

(51) Int. Cl.
*G01N 33/48* (2006.01)
*G16B 99/00* (2019.01)
*G01R 33/46* (2006.01)
*G01N 24/08* (2006.01)
*G06G 7/58* (2006.01)
*G16B 40/00* (2019.01)

(52) U.S. Cl.
CPC ............. *G16B 99/00* (2019.02); *G01N 24/08* (2013.01); *G01R 33/4625* (2013.01); *G16B 40/00* (2019.02)

(58) Field of Classification Search
CPC .......... G06F 19/18; G06F 19/22; G06F 19/24; G01N 33/66; G01N 33/582
See application file for complete search history.

(56) References Cited

U.S. PATENT DOCUMENTS

| | | |
|---|---|---|
| 4,689,564 A | 8/1987 | Leue et al. |
| 6,339,950 B1 | 1/2002 | Bengsch et al. |
| 6,584,413 B1 | 6/2003 | Keenan et al. |
| 2004/0181351 A1 | 9/2004 | Thompson et al. |
| 2009/0093010 A1 | 4/2009 | Nickerson et al. |

FOREIGN PATENT DOCUMENTS

| | | |
|---|---|---|
| DE | 19727879 A1 | 2/1999 |
| DE | 102005026133 A1 | 12/2006 |
| DE | 69937368 T2 | 7/2008 |
| WO | 0037944 A1 | 6/2000 |
| WO | 03017177 A2 | 2/2003 |

OTHER PUBLICATIONS

Carrola et al., "Metabolic Signatures of Lung Cancer in Biofluids: NMR-Based Metabonomics of Urine," Journal of Proteome Research, Nov. 8, 2010, pp. 221-230, vol. 10, No. 1.
Costello et al., "Citrate in the Diagnosis of Prostate Cancer," The Prostate, 1999, pp. 237-245, vol. 38.
Kim et al, "Toxicometabolomics of Urinary Biomarkers for Human Gastric Cancer in a Mouse Model," Journal of Toxicology and Environmental Health, Part A, 2010, pp. 1420-1430, vol. 73.
Kolker et al., "Metabolism and Bioenergetics: Methylmalonic Acid, a Biochemical Hallmark of Methylmalonic Acidurias but No Inhibitor of Mitochondrial Respiratory Chain," Journal of Biological Chemistry, Nov. 28, 2003, pp. 47388-47393, vol. 278, No. 48.
Lentz et al., "Metabolic Markers of Neuronal Injury Correlate with SIV CNS Disease Severity and Inoculum in the Macaque Model of NeuroAIDS," Magnetic Resonance in Medicine, 2008, pp. 475-484, vol. 59.
Saric et al., "Panorganismal Metabolic Response Modeling of an Experimental Echinostoma caproni Infection in the Mouse, Journal of Proteome Research, Jun. 2, 2009, pp. 3899-3911," vol. 8, No. 8.
Ong et al., "Metabolic profiling in colorectal cancer reveals signature metabolic shifts during tumorigenesis," MCP Papers in Press, Feb. 10, 2010, 42 pages.
Weinhouse et al., "On Respiratory Impairment in Cancer Cells," Science, Aug. 10, 1956, pp. 267-272, vol. 124.
Zhou et al., "Molecular Bases of Disease: Involvement of Oxidative Stress in the Relapse of Acute Myeloid Leukemia," The Journal of Biological Chemistry, Mar. 16, 2010, pp. 15010-15015, vol. 285, No. 20.
Lee et al., "CYP1A2 Activity as a Risk Factor for Bladder Cancer", Journal of Korean Medical Science, Dec. 1994, pp. 482-489, vol. 9 No. 6.
Ralph et al., "The Causes of Cancer Revisited: 'Mitochondrial Malignancy' and ROS-induced Oncogenic Transformation—Why Mitochondria are Targets for Cancer Therapy", Molecular Aspects of Medicine, 2010, pp. 145-170, vol. 31.

(Continued)

*Primary Examiner* — Eric S Dejong

(74) *Attorney, Agent, or Firm* — The Webb Law Firm

(57) ABSTRACT

A method for characterizing a sample is disclosed, having the following steps: providing at least one analysis result having a plurality of values, wherein the analysis result was generated by the analysis of a sample by at least one analysis method; determining the value of at least one mathematic relation between at least two values of the plurality of values; generating a characterizing signature of the sample on the basis of the value of the at least one mathematic relation. Furthermore, a method for characterizing a system is disclosed in which method the preceding method is used.

13 Claims, 25 Drawing Sheets

(56) References Cited

OTHER PUBLICATIONS

Gillespie et al., "Biomarkers in renal transplantation", Biomarkers in Medi, 2008, pp. 603-612, vol. 2, No. 6, Future Medicine, UK.

Gwinner, "Renal transplant rejection markers", Journal of Urology, 2007, pp. 445-455, vol. 25, No. 5.

Monnerjahn et al., "Analysis of Kidney Function Markers by 1H-NMR Spectra of Blood Plasma Using Class—and Attribute Planes of Self-Organizing Maps", Proceedings of the International Society for Magnetic Resonance in Medicine, Apr. 18, 1998.

Nickerson, "Post-transplant monitoring of renal allografts: are we there yet?", Current Opinion in Immunology, 2009, pp. 563-568, vol. 21, No. 5.

Pfahlert et al., "NMR-methode enables kidney diagnostics without biopsy", Labor Praxis, Aug. 8, 2015, pp. 1-2.

Chan et al., "Metabolic Profiling of Human Colorectal Cancer Using High-Resolution Magic Angle Spinning Nuclear Magnetic Resonance (HR-MAS NMR) Spectroscopy and Gas Chromatography Mass Spectrometry (GC/MS)", Journal of Proteome Research, 2009, pp. 352-361, vol. 8.

Kurhanewicz et al., "Combined Magnetic Resonance Imaging and Spetroscopic Imaging Approach to Molecular Imaging of Prostate Cancer", Journal of Magnetic Resonance Imaging, 2002, pp. 451-463, vol. 16.

Medina et al., "Histamine, Polyamines, and Cancer", Biochemical Pharmacology, 1999, pp. 1341-1344, vol. 57.

Sutcliffe et al., "Use of classical and novel biomarkers as prognostic risk factors for localised prostate cancer: a systematic review", Health Technology Assessment, 2009, 260 pp., vol. 13: No. 5.

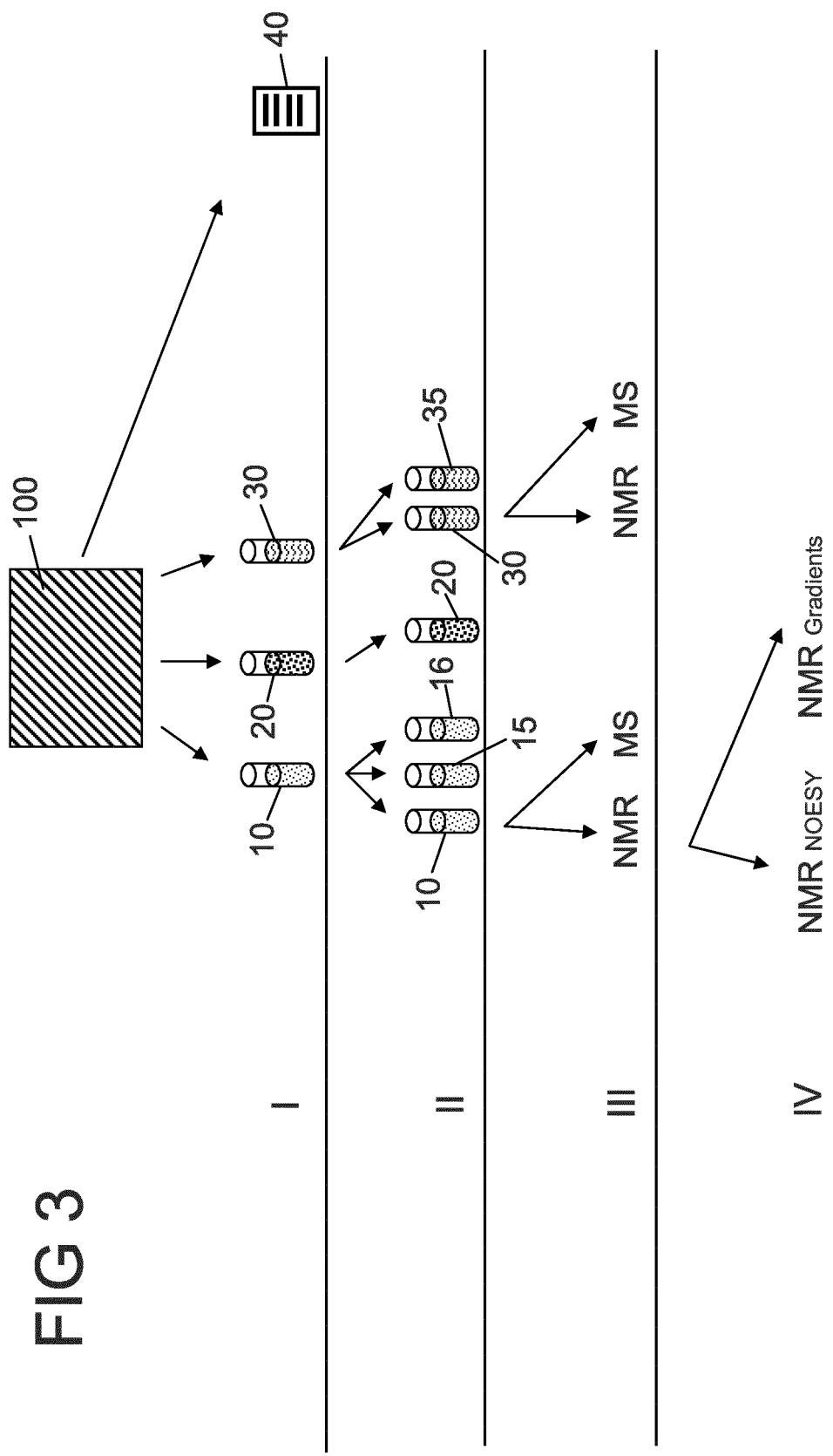

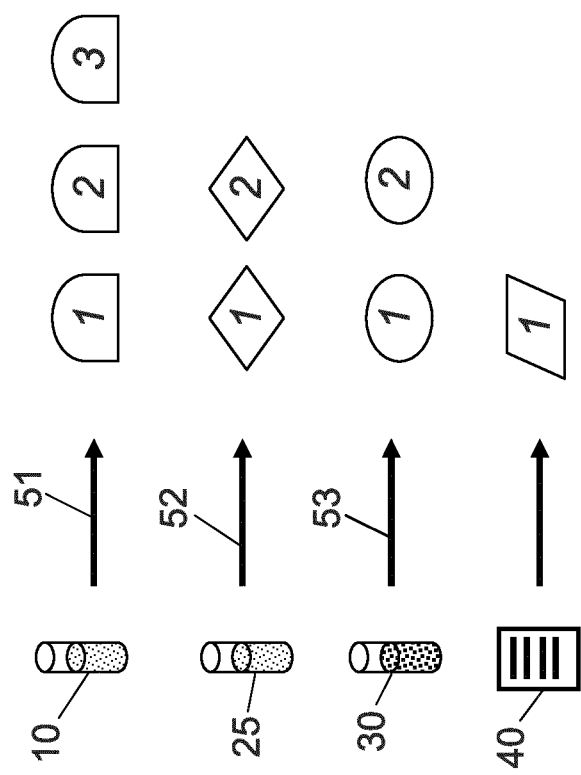

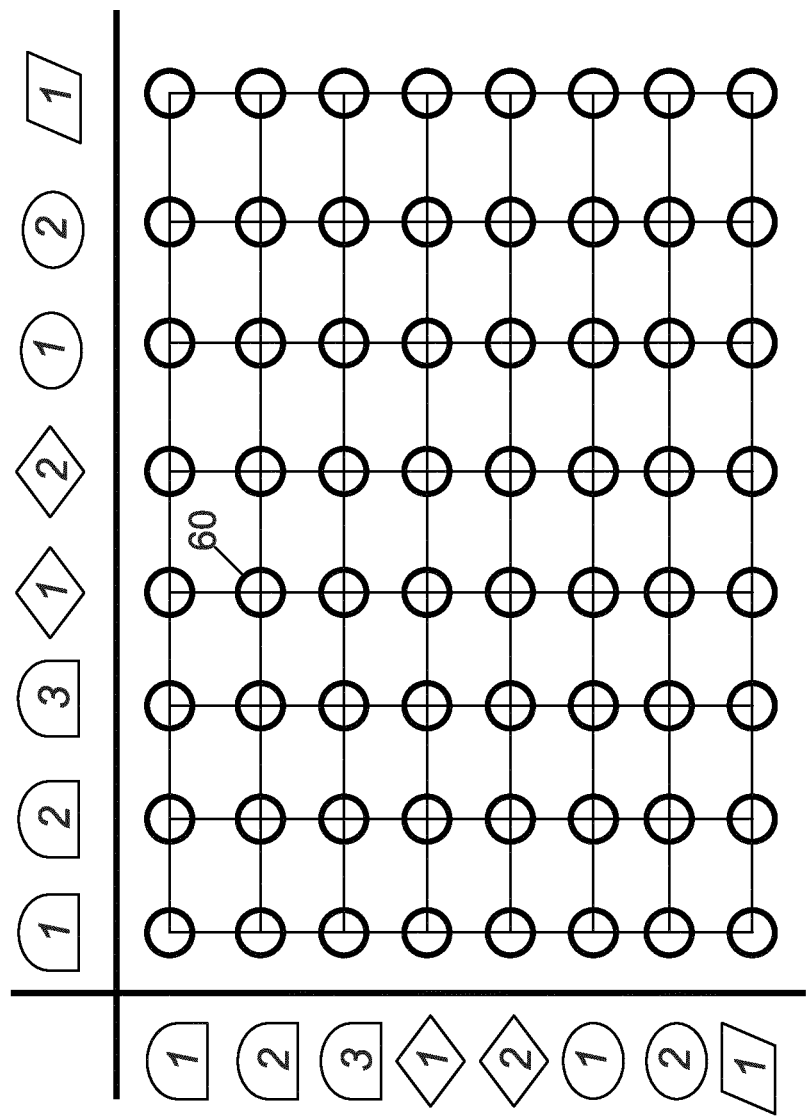

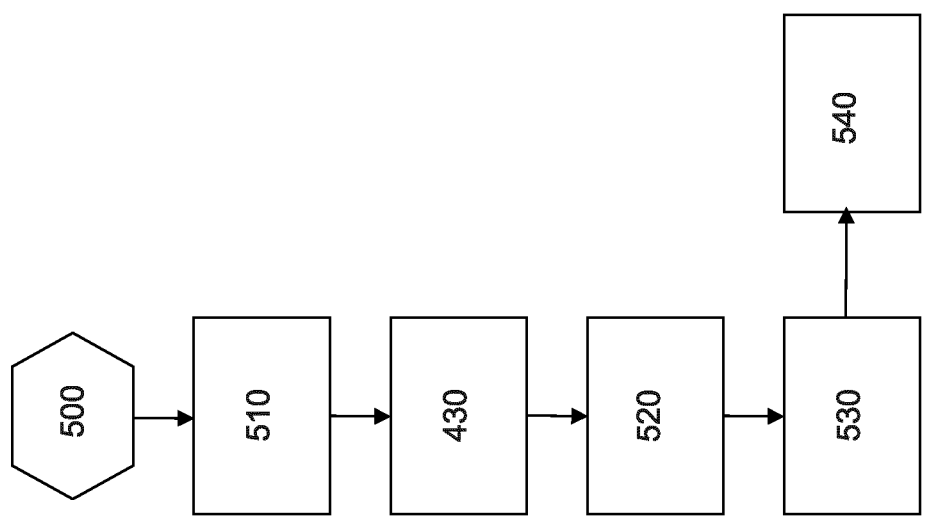

Significant correlations between the assigned substances.

| Number | Assignment (substance) | Correlation |
|---|---|---|
| 1 | methyl malonate (?) | |
| 2 | lactate | |
| 3 | methyl succinate | |
| 4 | p-cresol | |
| 5 | 3-hydroxy isovalerate | |
| 6 | citrate | |
| 7 | methyl guanidine | |
| 8 | malonate | |
| 9 | malonate | |
| 10 | taurine | |
| 11 | methyl guanidine | |
| 12 | taurine | |
| 13 | PAG | |
| 14 | trigonelline (?) | |
| 15 | α-glucose | |
| 16 | acetyl carnitine | |
| 17 | PAG / phenyl acetate | |
| 18 | PAG / phenyl acetate | |
| 19 | hippurate | |
| 20 | hippurate | |

METHOD FOR CHARACTERIZING A SAMPLE BY DATA ANALYSIS

CROSS-REFERENCE TO A RELATED APPLICATION

This application is a United States national phase of International Patent Application Number PCT/EP2011/067383, filed Oct. 5, 2011, which claims priority of German Patent Application Number 10 2010 038 014.8, filed on Oct. 6, 2010, and U.S. Provisional Patent Application No. 61/391,317, filed on Oct. 8, 2010, the disclosures of which are incorporated herein in their entireties by reference.

BACKGROUND OF THE INVENTION

Field of the Invention

The present invention relates in an aspect to a method for characterizing a sample, in another aspect to a method for characterizing a system and to related subject-matter.

Description of Prior Art

From prior art, different methods for analyzing measuring data of for example spectroscopically obtained data are known. In the known methods, generally the single signals of a substance are analyzed which signals are caused by this substance in the according measuring method. It is also known to pool different single signals in predetermined categories in order to achieve a simple data handling or a data reduction. In case of nuclear magnetic resonance spectroscopy (NMR spectroscopy) as measuring method, the single NMR signals are regularly assigned to the respective substances by which the signals are caused before a further analysis is carried out. Statistical NMR methods are also known in which no previous signal assignment is carried out.

In order to achieve more reliable conclusions, it is usual in prior art to use either single or a plurality of measuring signals for further analysis. If for example the body fluid of an individual is examined, this has the disadvantage that variations of the composition of the body fluid resulting for example from the nutritional status of the individual are also detected. Without exact knowledge of the nutritional status, a corruption of the measuring results occurs since single substances having a high concentration are also detected, although this only reflects a temporary concentration peak which is not representative for the general state of the individual.

Additionally, it is problematic in the analysis methods known from prior art that it is worked with a limited number of discrete values based on which then a conclusion to the status of the individual examined in each case is made.

SUMMARY OF THE INVENTION

It is an object of the present invention to overcome the pre-mentioned disadvantages of prior art and to indicate in particular a reliable and easily realisable method for characterizing a sample and a system.

This method is achieved by a method having the following method steps:
  providing at least one analysis result having a plurality of values, wherein the analysis result was generated by the analysis of a sample by at least one analysis method, determining the value of at least one mathematic relation between at least two values of the plurality of values, generating a characterizing signature of the sample on the basis of the value of the at least one mathematic relation.

In other words, a so-called signature is generated by a method according to an aspect of the invention, the signature being able to characterize the sample on the basis of a previously obtained measuring result, wherein it is not looked on single values or signals of the measuring result, but always on the value of a mathematic relation between at least two signals or values of an according analysis result. Thereby, these signals or values are such signals which are caused by one or several substances which are originally assigned to the analysed sample (thus, originally being contained in the sample) and are not added to the sample perhaps for normalisation purposes prior to carrying out the analysis.

During execution of this method, it is not necessary to firstly assign substances, by which the values or signals are caused, to certain values or signals of the analysis result. Thus, it is not necessary to assign a substance like perhaps lactate which causes a signal A to this signal A. Rather, it is possible and envisaged to carry out the method without such a previous assignment. The signal A is then set into a mathematic relation with signal B (the causing substance of which needs also not to be known), and the value X of this mathematic relation is further processed although it is still unclear, which substances have caused the signals A and B. In this manner, it is possible to draw upon a wealth of information which is instantly measured at the same time and is also available for evaluation. Thus, the method according to an aspect of the invention enables a highly precise evaluation of the analysis result also without correlation between substance and according signal in the analysis result. The analysis result can thereby be for example a spectrum, a chromatogram or a comparable result.

By drawing upon signals caused by unknown or at least not defined substances, also metabolites or substances not having been described in connection to a specific question of characterizing are considered in the method. Thereby, the informative value of the obtained signature and at the end of the whole characterisation is significantly increased. Because if one limits oneself to known substances or signals assigned to known substances for the characterization, one would possibly ignore a substance being equally good or even better suited for characterizing. Thus, the method enables reliable characterization on the basis of an unlimited and therewith unbiased data recourse independent on the actual state of knowledge and research.

In an embodiment, the plurality of values, out of which the values are chosen for determining the value of the mathematic relation, originate from exactly one analysis result (i.e. always e.g. 2 values of a single analysis result are set into relation to each other). It is possible to combine values of the mathematic relation originating from different sets of values (i.e. from different analysis results) for generating a single signature.

In an embodiment, the signature is not only based on single lines or bands of a spectrum, but on substances causing those lines and or bands. To be more specific, "based on substances" is to be understood as based on a parameter that is proportional to the concentration of the respective substance. E.g. a set of lines and their corresponding integrals could be such a parameter on which a signature might be based.

In a variant of the method, a mathematic editing of the analysis result is carried out in order to be able to describe it with a sum of single functions. In this manner, a continuous portfolio of values is generated so that, in contrast to prior art, no recourse to discrete values of the analysis result is necessary. In doing so, for example a mathematic iterative decomposition of the obtained analysis result into sets of lines can be carried out which can reproduce the original analysis result. A suited method is a spectral deconvolution. Subsequently, a superordinated set of lines can then be generated from all analysis results in order to pool into clusters and to filter the information contained in the different analysis results. By a deconvolution of different spectra, a noise reduction is also possible.

In a variant of the method, the sample which is analysed and characterized comprises a body fluid of an individual, a culture medium, seeds, a plant extract or food. In particular, the sample represents one of the pre-mentioned substances. Examples for a suited body fluid are blood, urine, bile, tissue fluid, sperm, lymph, saliva or cerebrospinal fluid. Examples for a culture medium are media usually used for growing bacteria which media can also be used in a fermenter. Examples for seeds are single or a plurality of seed grains out of which new plants can originate. Examples for a plant extract are extracts, generated with a suited extractant, of parts of a living or dead plant, for example extracts obtained from roots, leaves, fruits, the cortex or a comparable plant part. Furthermore, extracts obtained from seeds are also to be understood as plant extracts within the meaning of the present application. Examples for food are sausage, meat and milk products, fruit juices or fruit juice concentrates, wine, beer, other alcoholic and non-alcoholic beverages as well as convenience products.

In a variant of the method, the analysis method is chosen from the group consisting of NMR spectroscopy, mass spectrometry, electron spin resonance, vibrational spectroscopy, UV/VIS spectroscopy, fluorescence spectroscopy and X-ray spectroscopy. A suited example for vibrational spectroscopy is infrared spectroscopy, in particular using infrared radiation from the medium infrared range. If any of the pre-mentioned analysis methods is used in the characterizing method, the analysis result is a spectrum.

NMR spectroscopy is particularly well suited as analysis method. It is possible to work over a very broad measurement range by NMR spectroscopy, namely over more than six orders of magnitude (concentration of the substance in the analysis sample approximately 1 µmol/l to 1 mol/l). Further, hundreds of substances and substance concentrations are detected in parallel in only a single measurement. Thereby, the accuracy is better than 1% over the whole measurement range. It is particularly favourable that also unexpected ingredients of the sample are detected so that it is not necessary to know already prior to the analysis which substances one wants to detect. In case of a human urine sample, it can be drawn upon more than 1500 single signals by an NMR spectroscopic analysis, which signals in each case represent single, pure, quantifiable conditions.

To enable a particularly precise characterization of the sample, the sample is analysed in a variant of the method by at least two analysis methods. This means that the sample is initially analysed by one analysis method, for example by NMR spectroscopy. Subsequently, the sample is then analysed by a further analysis method, for example by mass spectrometry. Thereby, the analysed sample can be exactly the same sample in each case or a different aliquot of the same sample in each case. As long as the sample or its composition is not compromised by the first analysis method, one comes by both courses of action to the same result.

In a further variant of the method, the sample is indeed analysed by the same biophysical measuring method (that means exactly one analysis method is used), but the parameters in this analysis method are varied. This means, a variation of the measuring conditions or the measuring course takes place. Thus, a sample (or an aliquot of a sample) can for example be subjected to a first NMR spectroscopic analysis with a first set of measuring parameters, in order to be subsequently subjected to a second NMR spectroscopic analysis with a second set of measuring parameters. In this manner, it is possible to extract also with a single analysis method different information contents out of one and the same sample (or different aliquots of the same sample). For example, detailed information on the size distribution of lipoproteins in the serum (a so-called lipoprotein profile) can thus be obtained, in particular by NMR spectroscopy. Further, also analyses with respect to unsaturated fatty acids and further lipid components as well as to phospholipids are possible. Generally, the analysis method can be adjusted by different measuring parameters to a more sensitive detection of big or small molecules in each case.

To take advantage of the information generally contained within a sample as good as possible, it is further possible in another variant of the method to provide several samples and subject these samples to different preparation steps. This means, a variation of the sample preparation takes place. In this manner, certain components of the samples can be enriched in the desired manner, depending on the preparation or processing step, in the partial samples differently treated in each case. Subsequently, an analysis result being tailor-made with respect to the respective needs can be achieved by a suited choice of one or several analysis methods (optionally under variation of the measuring parameters).

To increase the informative value of the characterization even more, a plurality of values of the mathematic relation between two values of the analysis result in each case are determined in a variant of the method. This means, two values of the analysis results are put in mathematic relation to each other in each case. The result is a value of this mathematic relation. The more pairs of two values of the analysis result are used, the more values of the according mathematic relation are obtained. Additional information remaining otherwise unconsidered can be obtained from the analysis result by such an increased correlation of values of the analysis result.

In a further variant of the method, each value of the analysis result is correlated with each other value of the analysis result to obtain in this manner a plurality of values of a mathematic relation between two values in each case. In this manner, for example a 2×2 matrix, a 3×3 matrix, a 4×4 matrix, a 5×5 matrix etc. can be generated from the values of the mathematic relation. The size of the matrix is dependent on the number of the considered values of the analysis result. Thereby, for example, a threshold value can be given that determines whether a signal of the analysis result, to be detected in numbers, is also considered as value. Such a threshold value can thus control of how many values to be considered the analysis result consists.

The effect of such proceeding dimensioned for a correlation of values as comprehensive as possible is that the maximum possible information is extracted out of the analysis result. However, this is connected to an increased calculation effort. If the calculation effort is to be kept low, it is advisable to work only with a subset of all possible values of the mathematic relation between the respective values of the analysis result. Thus, in a variant of the method, a subset of the plurality of values of the mathematic relation is chosen which is then used for generating the characterizing signature.

In a further variant of the method, the mathematic relation is the ratio of the respective values to each other. The value of the mathematic relation is in this case the value of the quotient. Thereby, it can be achieved in a particularly simple manner that concentration differences of single substances which are caused, for example, by a different nutritional state or other physical circumstances of the respective individuals, from whom the samples originate, are eliminated. This is in particular the case if different nutritional states or other physical circumstances have the same or at least comparable effects on the concentrations of at least two substances (and therewith also on the signals in the analysis result caused by them). Thus, by coupling substances which are affected by an external or internal influence in the same manner, although they are to be assigned to different metabolic pathway and should be thus rather behave independent on each other, statistic effects are eliminated which would be otherwise observed. Further, a significantly higher specificity than hitherto possible can be achieved in the diagnostic area by this generation of a ratio in a particular simple manner.

Afterwards, a characterizing signature can be generated on the basis of several values of such ratios—but also on the basis of several values of other mathematic relations—which signature subsequently enables, for example, in comparison to at least one single further already existing signature a classification of the individual, from whom the sample originates, into a certain group, like for example "normal" or "pathological". Thus, by a comparison with collectives exhibiting a pronounced response to a certain problem, an assignment of a sample to one of those collectives on the basis of the characterizing signature can be carried out.

In other words, the characterizing signature is based on a mathematic relation of values of an analysis result (like NMR signal intensities or integrals). The characterizing signature can be depicted as a matrix. In an embodiment, most values of the matrix have the value zero. A distinct signature differs from another distinct signature on the one hand by the pattern of values differing from zero and on the other hand by the specific quantitative (numeric) value of those values differing from zero. There exist different possibilities for generating the signature. An exemplary possibility will be explained hereinbelow in connection to exemplary embodiments. It is to be understood that the disclosed techniques of generating the signature are not limited to the specific exemplary embodiments but can rather generally be applied for all examined problems.

As already mentioned, it is not necessary to assign substances being causative for the values of the analysis result to those values of the analysis result which are used for generating the characterizing signature. In other words expressed, it is possible to work blindly. This means, it is possible to generate the signatures without knowing which substances are causative for the observed signals and finally find an expression in the signature. The logic underlying the signature generation can thus be based on not-denominated or not-determined measuring variables that are, however, anchored in the metabolism of the examined individual. By a signature generation without assignment of substances, certain conditions of the examined individual can be recognized also without a complete disclosure of the relationships anchored in the metabolic pathways. This results in an almost unlimited broad spectrum of application of the instant method. In a variant of the method, it is wilfully refrained from such an assignment of substances to signals or to values of the analysis result. This reduces the effort of the whole analysis monumentally and suppresses laborious works which are necessary for such an assignment. Although the correlation between substances and signals caused by them in an analysis result can be of interest from a scientific or academic point of view, such a correlation is not necessary for the instant method. Nonetheless, the method can also be carried out if an according assignment of substances to according signals has already taken place.

The object underlying the invention is, in an aspect, also achieved by a method for characterizing a system exhibiting the following steps:
 providing at least one sample taken from a system,
 analyzing the sample by at least one analysis method in order to generate at least one analysis result,
 carrying out a method according to the preceding explanations on the sample taken out, in order to generate a characterizing signature of the sample,
 comparing the signature of the sample with at least one comparative signature which was generated as a signature of a comparative sample,
 determining a deviation between the signature of the sample and the at least one comparative signature and
 assigning the signature and the determined deviation to the system.

This means that by comparing the signature of the sample with the comparative signature of a comparative sample a whole system can be characterized with this method, for example, by classifying into a certain group. The method steps for characterizing a sample explained above are thereby inherent components of the method for characterizing a system. Thereby, in particular, also the signature of the comparative sample is determined with a method for characterizing a sample according to the preceding explanations.

"Characterizing" is to be understood in particular as the determination of the health status of an individual, the determination of the risk of an organ rejection after a transplantation, the determination of the organ function after an organ transplantation or organ damaging, the efficiency of an installation, a quality control, a purity test, a determination of fitness within the framework of a development of an active agent, an optimization for culture purposes, a clarification of origin or a quality assurance. Suited organs for the pre-mentioned characterisation possibilities are for example liver, kidney, spleen, lung and heart, in particular the kidney.

The health status of an individual can be, e.g., the development of a disease, in particular if the individual is subjected to a therapy. Thus, the efficacy of the therapy can be monitored. In an embodiment, the disease is a tumour-associated disease like prostate carcinoma, cancer of the colon, lung cancer, kidney cancer, pancreas cancer, liver cancer and stomach cancer.

Within the framework of quality control, in particular of a quality control of raw materials, it is for example possible to clarify the question whether certain plant ingredients are present in sufficient amount and quality also after longer storage.

Within the framework of purity tests, for example a differentiation regarding substances having allergenic potential can take place or an examination whether such a differentiation is possible.

Within the framework of a development of an active agent, it can be examined which vegetable agents could be interesting for pharmaceuticals and how they can act upon the human metabolism.

Within the framework of an optimization for culture purposes, it can be examined which plants or which seeds should be used in a targeted manner in culturing regarding desired ingredients.

Within the framework of a clarification of origin or quality assurance, it can for example be determined whether seed has been correctly declared, whether the indicated variety is present and whether there are impurities in the examined sample.

A characterizing signature can also be used for an automatic total quantification of a spectrum, as far as a known or predetermined amount of a standard is present in the examined sample. In case of NMR spectroscopy as analysis method, a signal of defined height is caused by the predetermined amount of the standard (or another substance), the signal corresponding to a certain amount or number of protons. If now another known substance is present in the sample, also its amount can be determined since the number of protons for a molecule of this substance is known if the substance as such and its chemical structure are known. Consequently, the known substances contained in the sample can be quantified by co-measuring a standard.

In order to enable the previously mentioned classification of the sample into a certain group, the method exhibits in a variant a further step in which the classification of the system into a predetermined category on the basis of the deviation between the signature and the comparative signature takes place. Such a classification can for example be effected by a support vector machine, wherein, in an embodiment, no digital algorithm but an analogue algorithm is used to be able to detect intermediate conditions between single categories.

In a further variant of the method at least one further parameter of the system underlying the comparative signature is used for classifying the system. This further parameter can also be denominated as external parameter. Examples for such a further parameter are for example the properties "healthy" or "pathological" or—in particular regarding a biogas plant as system to be analyzed—"efficient plant" or "inefficient plant". By knowing such a further parameter of the comparative system, for which the comparative signature was generated, it is possible to assign the actually analyzed system on the basis of its signature also to the category or class or group of the comparative system or to another group or class or category. Thus, it can be estimated from the, for example, vectorial depicted deviation of the signature from the comparative signature how strong and in which direction the signature deviates from the comparative signature in order to be then able to perform an according adjusted classification.

In a further variant of the method, the characterizing system is a biological system or an industrial system representing a biological process or a substance resulting from a biological system. Examples for a biological system are a multi-cellular animal, in particular a mammal like a human or an non-human mammal, further single cells or monocellular creatures like bacteria, further viruses, fungi and plants. Examples for an industrial system representing a biological process are a waste water treatment plant, a biogas plant, a technical fermentation process and a biotechnological plant. Examples for the substance resulting from a biological system are seed, food of natural origin like fruit juice, milk products as well as meet and sausage goods or convenience products.

To achieve a qualitatively particularly suited characterizing of a system, different samples of a system are, in a variant of the method, analyzed individually or in combination to each other. For example, different body fluids of an individual or also differently conditioned samples of the same body fluid of an individual can serve as different samples of a system. Of course, also different body fluids can be processed or analyzed in several different manners in each case in order to thus represent different samples of a system. Thus, provision is made in this variant that, for example, a blood sample and a urine sample of an individual are examined by the same analysis method or by different analysis methods. Thereby, the blood sample and the urine sample can be taken from the individual for example at the same time or with a small temporal distance in order to essentially represent the same condition of the individual.

In order to design the characterization of the system in another manner even finer and in particular to be able to classify the system simpler into a predetermined category, a supplementary parameter of the system is additionally used in a variant of the method in order to generate the signature of the sample. Such a supplementary parameter can for example be a physiological parameter of the individual from whom the sample originates. Examples of such a physiological parameter are the blood pressure of the examined individual or its body mass index. Thus, this is an external parameter. Such an external parameter is a variable which was not determined by the technique underlying the analysis method or another comparable technique, but characterizes the system or individual independent on the sample.

The use of certain substances as marker for determining the risk of a kidney rejection in an individual in whom a kidney transplantation has been carried out is also a subject-matter of an aspect of the present invention. Thereby, the substances used as marker either individually or in any arbitrary combination are methyl malonate, lactate, methyl succinate, p-cresol, 3-hydroxy isovalerate, citrate, methyl guanidine, malonate, taurine, methyl guanidine, phenyl acetyl glycine (2-(N-phenyl acetyl) amino acetic acid), trigonelline, α-glucose, acetyl carnitine, phenyl acetate and hippurate.

A subject-matter of an aspect of the invention is also the use of certain other substances for monitoring the course of a therapy against a tumour. The substances to be used as such marker either individually or in any arbitrary combination are citrate, creatinine, malonate, methyl malonate, methyl guanidine, dimethyl succinate, hydroxy isovalerate, tartrate, salicylate, hypoxanthine, hydroxy butyrate, allothreonine, 1-methyl urate, trimethylamine-n-oxide, glycolate, 5-hydroxy methyluracil, 3-hexene dione acid, xanthine, formate, fatty acid (derivate), histamine, dimethyl aminopurine and benzoate.

In this context, exogenic substances (i.e. substances externally applied to an examined individual, e.g. due to a medication) like benzoate, salicylate and tartrate are also well suited as marker since they can be metabolized in the body of an individual in a different way or not at all in dependence of the development of the disease or the therapy, respectively.

In an embodiment of the disclosed uses, use of at least two substances is particularly suited. Thereby, in an embodiment, interrelated substances (as can be seen from the tables and Figures explained hereinafter below) are used in connection to each other.

In a further embodiment, the tumour is chosen from the group consisting of prostate carcinoma, cancer of the colon, kidney cancer.

Subject-matter of an aspect of the invention is also the use of the described signature technique for monitoring the progression of a disease, in particular if the individual suffering from the disease is subjected to a therapy against the disease.

A subject-matter of an aspect of the invention is further a computer program product having a computer program which has a program code for carrying out any of the above-explained methods, if the computer program is executed on a computer.

In particular then, if the mathematic relation, the value of which serves as basis for generating the characterizing signature, is chosen in such a way that concentration differences of single substances compensate each other, thus it is possible to work independent on concentration, such computer program product enables waving an additional concentration determination of the substances in the sample to be analyzed. This is in particular the case if the mathematic relation is a division so that the ratio between two values of the analysis result is established. In doing so, the effort on a laboratory scale for characterizing the sample or the system is significantly reduced, whereby on the one hand time and on the other hand costs can be saved. Furthermore, the data amount for the further analysis is reduced by generating the value of the mathematic relation between the at least two values of the analysis result so that subsequent method steps can be effected with a significantly lower calculation effort than this is the case without an according calculation of the value of a mathematic relation. By these specific technical effects, the according computer program product can make applicable the methods explained above in further details in a very attractive manner.

Another subject-matter is a software for carrying out any of the above-explained methods. Such a software enables the automated execution of the explained methods. It can be used to analyze previously obtained measuring data or to also interact with a measuring device like a spectrometer for assisting the measurement of data.

The disclosed methods are not only suited to establish positive conclusions (like "This signature indicates that the sample belongs to group A."), but also negative conclusions (like "This signature indicates that the sample does not belong to group A, B, C, D."). Whereas positive conclusions are can be specifically drawn in 1-to-1 problems, negative conclusions are helpful in 1-to-n problems (n being a number higher than 1).

All of the above-explained possibilities of embodiments or variants of the single methods can be combined in any desired manner and can be applied both to the method for analyzing a sample and also to the method for analyzing a system.

Aspects of the present invention will be explained in further detail with the help of the subsequent Figures and examples.

BRIEF DESCRIPTION OF THE DRAWINGS

FIG. 3 shows a schematic depiction of a possible data acquisition from a biological system, FIG. 4A shows a first overview depiction for generating a characterizing signature, FIG. 4B shows a second overview depiction for generating a characterizing signature, FIG. 22 is a schematic flow-chart of an embodiment of a system for characterizing a sample and FIG. 23 is a schematic flow-chart of an embodiment of a system for characterizing a system.

FIG. 24 is a table depicting existing significant correlations between assigned substances.

DETAILED DESCRIPTION

Figure 1:
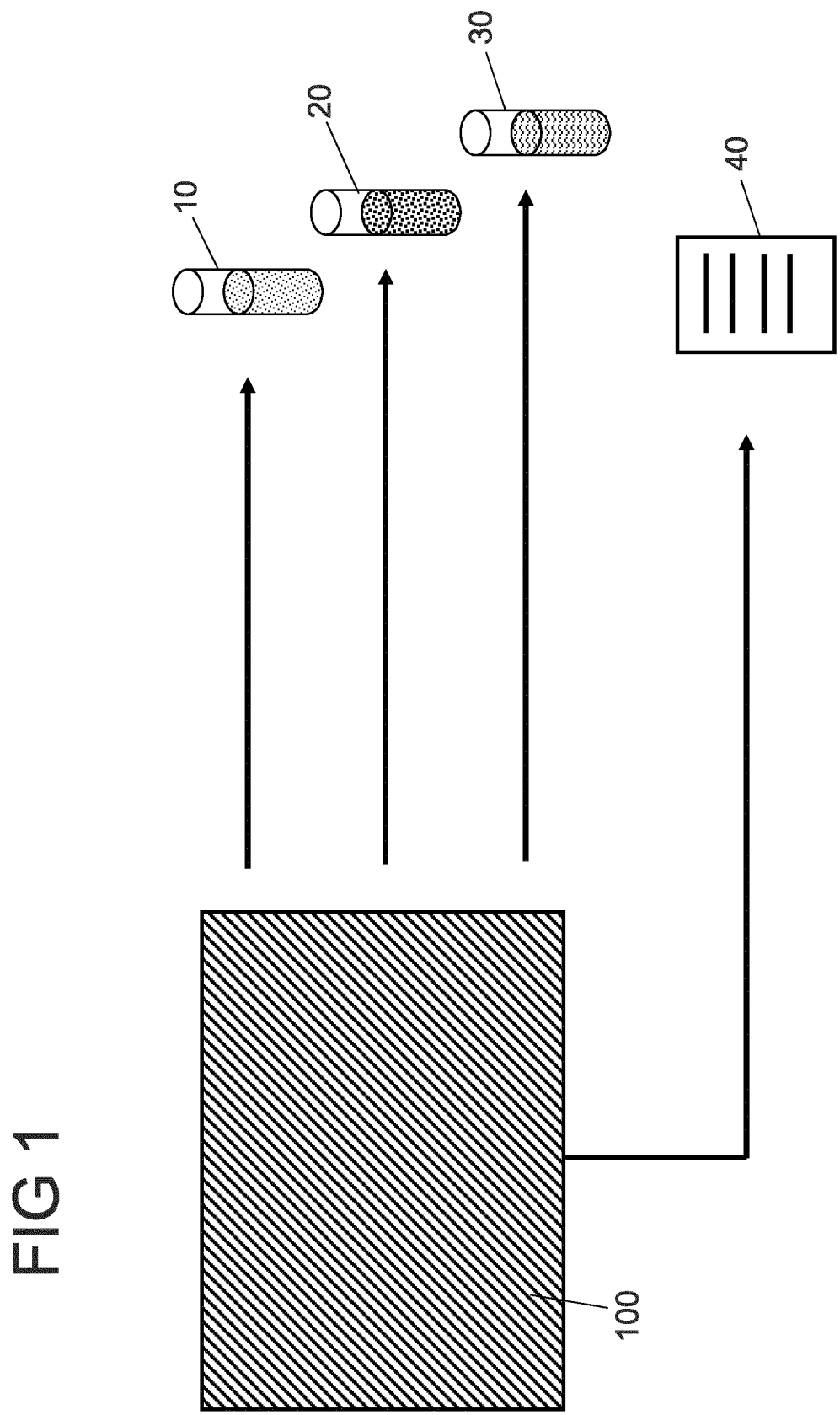
FIG. 1 shows a schematic depiction of an exemplary sampling of a biological system.

FIG. 1 shows a schematic depiction of sampling a biological system 100. The aim of sampling is to characterize the biological system 100 and to evaluate it in a stationary manner. Thereby, the characterization can be targeted to the actual state of the biological system 100 with respect to a given question. The question can for example be whether seeds originate from a variety A or from a variety B. A further question could be for example whether the biological system 100 works faultlessly at the time point of taking out the sample (this is in particular of interest with respect to a biogas plant).

The question can also be targeted to the future state of the biological system 100. The characterization of the biological system 100 can for example be targeted to determine whether the rejection of a transplanted organ is probable or not. A further possible question is whether a patient will come down with diabetes or a cardiovascular disease with a higher or lower probability. Yet another possible question is whether an intended drug administration or drug dosage will be efficient in a patient or not.

As depicted in FIG. 1, a first sample 10, a second sample 20 and a third sample 30 are taken from the biological system 100. Thereby, the number of samples is generally arbitrary and not limited to the top. The first sample 10 can be for example urine, the second sample 20 for example blood plasma and the third sample 30 another body fluid.

Furthermore, external measuring results 40 like for example the blood pressure or the body mass index of a patient can be taken from the biological system 100. The external measuring results 40 are thus measuring results which have been obtained by other methods than those methods which are used for characterizing the first sample 10, the second sample 20 and the third sample 30.

Within the framework of characterizing the biological system 100, the sampling of the biological system 100 represents the first level.

In the second level of the characterization, a variation of the sample processing can take place, if required. Samples consisting of blood plasma or serum can for example be measured without further processing, thus in the form in which they have been taken from the body. Thereby, it is for example also possible to determine the size distribution of the lipoproteins contained in the blood plasma or the serum by NMR spectroscopy.

The lipoproteins being present in the according samples can also be cleaved by the addition of detergents. In doing so, the possibility exists to measure the compositions of the lipids being present in the blood by NMR spectroscopy.

Figure 2:
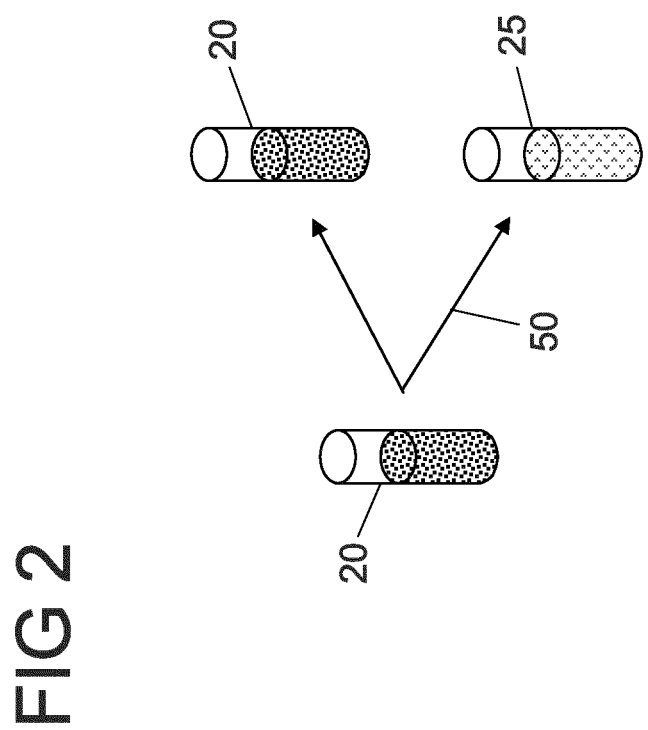
FIG. 2 shows a schematic depiction of possible variations in sample processing.

Such a possible variation of the sample processing is depicted in FIG. 2. Thus, here it is exemplarily indicated how the second sample 20 is transferred one time without further treatment (upper arrow) to the measurement of the lipoproteins contained in the second sample 20. In FIG. 2 it is further depicted that alternatively a detergent 50 can be added to the second sample 20, this resulting then in a treated second sample 25. The treated second sample 25 can then be used for measuring the lipids contained therein.

As third level in the characterization of the biological system 100, a possible variation in the measuring methods can take place. Different measuring methods have different strengths, error sources and dynamic areas. Thus, for example mass spectroscopy is markedly more sensitive than NMR spectroscopy. On the other hand, it is more difficult to work quantitatively with mass spectroscopy. By a combination of different methods it is possible to acquire markedly more and more significant data than this is possible with a single measuring method.

According to the questions and the substances to be examined in the samples, a different combination of different measuring methods is thus thinkable.

As fourth level in the characterization of the biological system 100, a variation in carrying out the technologies can further be effected. For example, blood plasma samples and serum samples can be examined with different NMR pulse programs. Furthermore, gradient edited spectra permit that information on proteins and lipoproteins (thus high molecular compounds) are measured, whereas metabolites having a lower molecular weight are suppressed.

In contrast, NMR CPMG spectra (CPMG denotes Carr Purcell Meiboom Gill; NMR CPMG is a NMR relaxation diffusion measuring method) indicate only low molecular components (regularly low molecular metabolites), whereas high molecular compounds are suppressed. Depending on the problem, a variation in carrying out the technique adjusted to the individual needs can here thus be effected.

This is possible in any desired combination for the first sample 10, the second sample 20 and the third sample 30. Thus, for each of these samples, for example a gradient edited NMR spectrum for high molecular compounds and/or an NMR CPMG spectrum for low molecular compounds can be acquired.

The data acquisition carried out within the framework of characterizing the biological system 100 is schematically depicted in FIG. 3. Thus, in the first level I the first sample 10, the second sample 20 and the third sample 30 are taken from the biological system 100 within the framework of sampling. Further, external measuring results 40 are taken out (confer in this respect also FIG. 1).

In the second level II, a variation of sample processing takes place. Starting from the first sample 10, an untreated first sample 10, a first sample 15 treated by a first method and a first sample 16 treated by a second method can thus be obtained by different sample processing techniques. Further, starting from the second sample 20, an untreated second sample 20 can be obtained without further sample processing. Starting from the third sample 30, further an untreated third sample 30 as well as a third sample 35 treated by an according sample processing can arise.

In the third level III, finally a variation of the measuring method takes place. Thus, for example each of the sample or partial sample obtained in the second level II can be subjected to different measuring methods like NMR spectroscopy and mass spectroscopy (MS).

In the fourth level IV, finally a variation of the measuring methods can take place which is depicted in FIG. 3 only exemplarily for NMR spectroscopy. Thus, here in the fourth level IV the acquisition of NOESY NMR and gradient NMR spectra is provided.

In FIG. 4A an overview over the first step for generating a characterizing signature is depicted. Thus, the first sample 10 is measured by a first method 51, resulting in a set of first values. This set of first values is depicted by the numbers 1, 2, 3 in a semicircle-like border strip. Further, a treated second sample 25 is measured by a second method 52, resulting in a second set of values. This second set of values is depicted by the numbers 1, 2 in a diamond standing on the apex.

Further, the third sample 30 is measured by a third method 53 resulting in a third set of values. This third set of values is depicted by the numbers 1, 2 in an ellipse.

Furthermore, the fourth value set being depicted by the number 1 in a diamond lying on the side can be extracted out of the external measuring results 40.

FIG. 4B gives now an overview over the second step of signature generating. For this purpose, the values obtained in the first step depicted in FIG. 4A are correlated to each other. This is depicted in FIG. 4B by a matrix. In this context, the numbers 1, 2, 3 and the different geometric forms denote the values of the first to fourth value set of FIG. 4A. This means, a "1" in a diamond standing on the apex denotes a value 1 obtained by the second measuring method 52. A "2" in the semicircular-like form denotes the value 2 from the measurement carried out by the first method 51. A circle is illustrated at the intersection between the single values in each case, the circle depicting a mathematic connection between the single values. In the present case, the mathematic connection or relation is a ratio between these values. Thereby, the values indicated in the line are to be considered as dividend and the values indicated in the column are to be considered as divisor. Consequently, the circles in the matrix of FIG. 4B represent the values of the mathematic relation between the single values obtained from the measurements. By these values, the according signature can be generated for characterizing the biological system 100.

For simplifying the depiction in FIG. 4B, only a single value 60 is provided with an according reference sign. This value 60 of the mathematic relation between the value 1 obtained with the second method 52 and the value 2 obtained with the first method 51 thus represents the value of the mathematic relation between those two values (value 1/value 2) and serves, like also the other values of the respective mathematic relations between the single measuring values, for generating the signature.

FIGS. 5 to 11 will be explained in more detail with the aid of the subsequently described first exemplary embodiment.

First Exemplary Embodiment: Kidney Rejection Test

200 μl of a buffer solution were added to 500 μl human urine. This buffer solution consists of a sodium phosphate buffer having a concentration of 800 mmol per liter and a pH value of 7.4, 300 μmol per liter sodium trimethylsilyl propionate (TSP) and 15% $D_2O$, wherein the nominal pH value was measured prior to $D_2O$ addition. Urine and buffer were mixed in an Eppendorf tube and centrifuged for 15 minutes at 4° C. and 17.900 rpm. 500 μl of the supernatant were transferred into a 5-mm NMR sample tube. Subsequently, an NMR measurement took place.

An NMR spectrometer of the type Advance II+600 having a TXI sample head was used for NMR measurement. The height of the sample tube in the spinner was 20 mm and the adjusted actual temperature 298 K. The maximum storage time of the sample at room/measuring temperature was four hours. The measurement was started when a sufficient temperature equilibration was present; this was the case if the temperature fluctuation of the sample was within ±0.2 K of the nominal temperature.

For the actual NMR measurement a parameter set was used which is depicted in subsequent table 1. By an NMR measurement with the according parameters an automatically processed spectrum was obtained for each sample. A phase correction, a baseline correction and a referencing were carried out during the automatic processing.

TABLE 1

Overview over the Parameters used during the NMR Measurement

| Acquisition (variable) | Acquisition (invariable) | Processing (invariable) |
|---|---|---|
| p1~10 μs | PI1: 0 dB | SI: 262144 (256 k) |
| pl9: 60 dB | TD: 98304 (96 k) | WDW: EM |
| o1: 2852.20 | NS: 64 | LB[Hz]: 0.3 Hz |
| | DS: 4 | PHC1: 0.0 |
| | D1: 4 s | PH_mod: pk |
| | AQ + D1: 8.09 s | |
| | RG: 16 | |
| | SWH: 12019.23 Hz | |
| | SW: (20 ppm) LOCNUC: 2H | |

Figure 5:
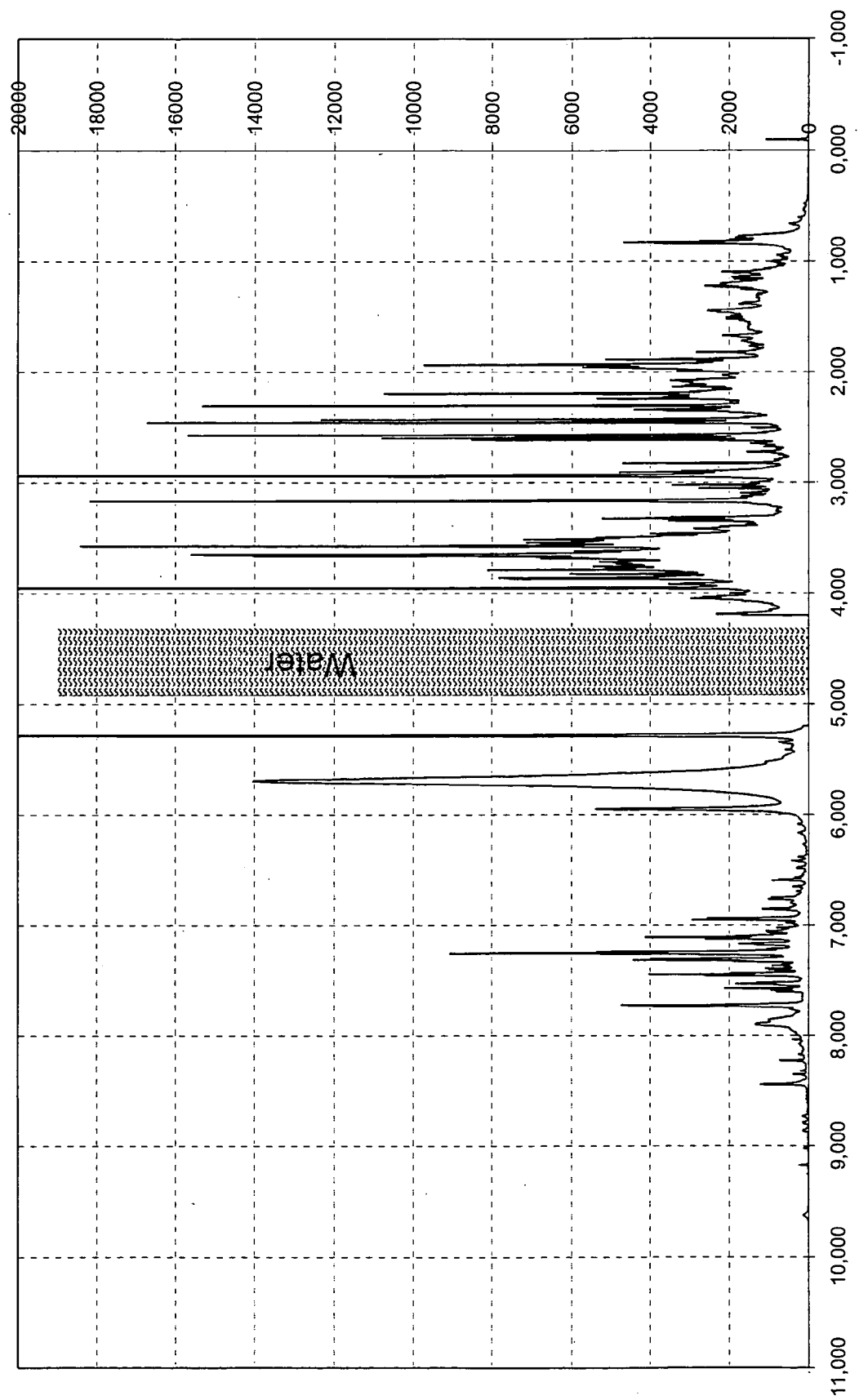
FIG. 5 shows an NMR spectrum of a human urine sample.

The respective processed NMR spectrum is depicted in FIG. 5. Thereby, the intensity on the y-axis is depicted in arbitrary units over the chemical shift in ppm on the x-axis. Signals lying in the range of resonances of water are suppressed. The according range is marked by a box in FIG. 5.

The NMR spectrum was now deconvoluted, that means transferred into Lorentz and Gauss lines. Subsequently, the spectrum was depicted in vectorized form so that the location of the line (of the signal), the line width, the integral and the configuration are accessible.

This method of sample processing, NMR measurement and measuring data processing was repeated for numerous further urine samples of other persons. As a result, numerous processed NMR spectra of different persons were present. The persons, the urine of whom was chosen for NMR measurement could thereby be assigned to two groups. On the one hand, there were persons showing a kidney rejection after kidney transplantation. On the other hand, the urine of persons was used who did not show a kidney rejection after kidney transplantation.

Figure 6:
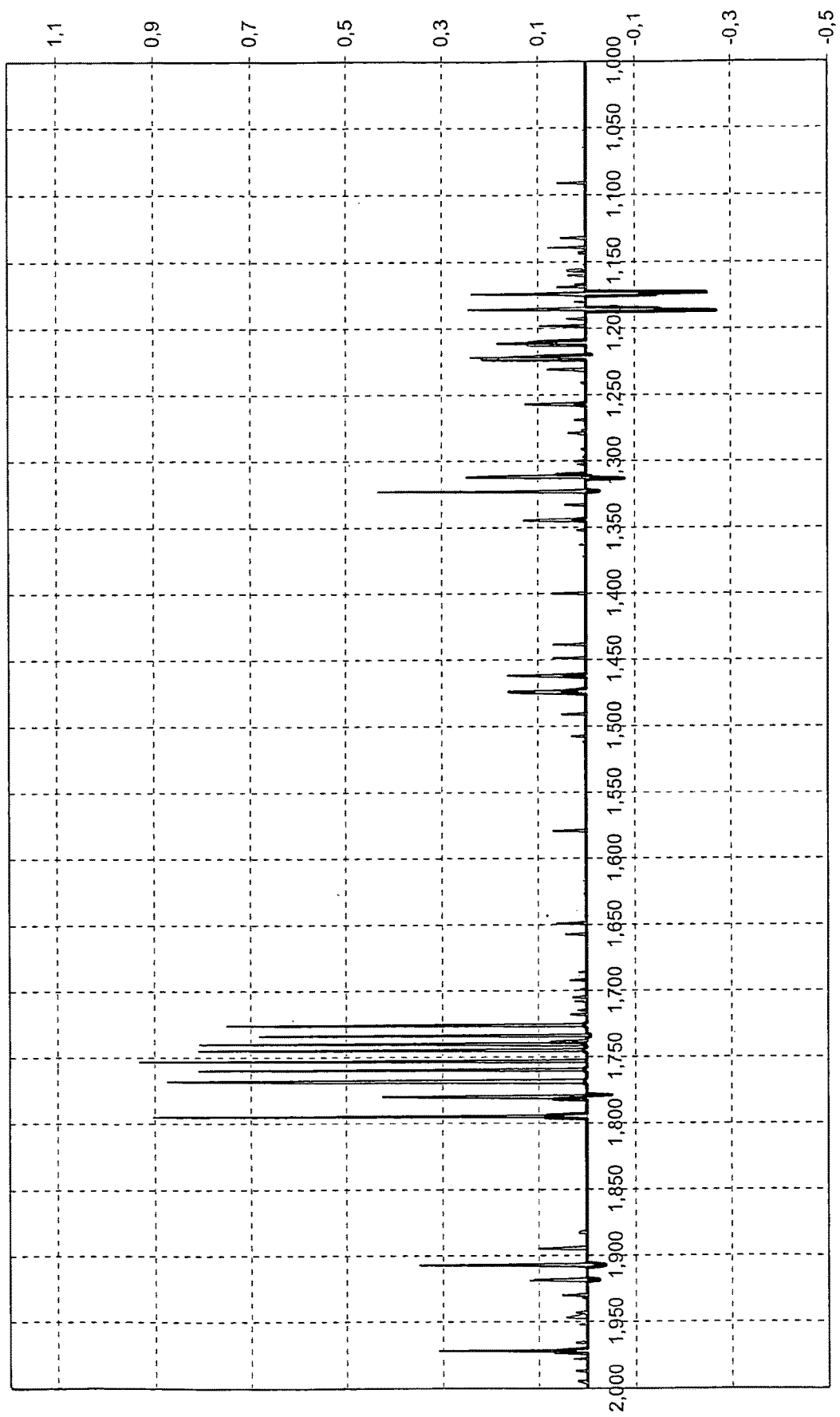
FIG. 6 shows a graphic depiction of normalized sums of NMR signals of urine samples of different persons.

To now generate a characterizing signature, in order to characterize the group "kidney rejection" from the group "no kidney rejection" on the basis of the obtained NMR spectra, on the one hand a normalized sum of signals of approximately 50 persons with kidney rejection and a normalized sum of signals of approximately 50 persons without kidney rejection was formed. Further, the difference of the normalized sums of both groups was determined. The result of this calculation is depicted in FIG. 6. Thereby, signal sums depicted in thin lines represent the group of persons with kidney rejection and the signal sums of persons without kidney rejection. The thick lines represent the difference between both groups. The percentage frequency distribution between the single signal sums gives a marked indication as to which signals in the respective groups could be meaningful for signature generating.

The twenty most peculiar signals were characterized by their position in the spectrum and their integral and transferred into a list. This list is depicted in the subsequent table 2.

TABLE 2

List of twenty peculiar signals

| Number | Signal position [ppm] |
|---|---|
| 1 | 1.174 |
| 2 | 1.310 |
| 3 | 2.132 |
| 4 | 2.198 |
| 5 | 2.330 |
| 6 | 2.513 |
| 7 | 2.767 |
| 8 | 3.096 |
| 9 | 3.105 |
| 10 | 3.222 |
| 11 | 3.378 |
| 12 | 3.394 |
| 13 | 3.779 |
| 14 | 4.386 |
| 15 | 5.223 |
| 16 | 5.601 |
| 17 | 7.335 |
| 18 | 7.396 |
| 19 | 7.551 |
| 20 | 7.828 |

Subsequently, a matrix was generated for each NMR spectrum (both for the group of persons with kidney rejection and for the persons without kidney rejection), in which matrix the twenty peculiar values previously determined were correlated in each case with each other. All matrix elements of the generated matrices were subsequently separately from each other added and normalized for the group of persons with kidney rejection and the group of persons without kidney rejection. As a consequence, two matrices were obtained, one of which representing the signature for the group of persons with kidney rejection and the other the signature of persons without kidney rejection. In the subsequent table 3, an according added and normalized correlation matrix for the group of persons with kidney rejection is exemplarily represented.

Most of the 400 values in the 20×20 matrix have no or only a low informative value. Therefore, now those matrix elements were chosen which essentially contribute to the distinction of both groups. This choice took place by firstly calculating a score according to the proceedings explained below for each signal of the previously added matrices. Subsequently, one of the 400 matrix values at a time was successively deleted from the respective matrix and the score of the respective matrix or signature was then re-calculated in each case. Prior to deleting a further value, the previously deleted value was added once again to the analyzed signature so that the analyzed signature always consisted in each validation step of 399 elements. If this deletion had no or only a very small effect onto the score, the value zero was assigned to the matrix value deleted in this validation step. If the deletion had a bigger effect on the score, a higher value was assigned to the according matrix value. A suited possibility for assigning a certain value to a matrix cell will be explained with respect to the third exemplary embodiment in more detail. Subsequently, an addition of the values assigned the single matrix values and an assignment of those sum values to the values of the matrix depicted in FIG. 3 took place. These assigned sum values are depicted in the subsequent table 4. The assigned or weighted sum values of meaningful matrix elements are thereby indicated in bold font.

During all of the precedingly explained method steps, no assignment between the peculiar signals and certain metabolites or substances being causative for those signals has yet taken place. Such an assignment is—as already explained above in detail—not necessary for signature generating. Nonetheless, such an assignment can be of scientific interest, for which reason it was presently carried out. In the subsequent table 5, an assignment of substances to the peculiar signals is depicted, the assignment being made on the basis of the obtained NMR spectra and comparative spectra. Substances marked with a question mark indicate that the assignment could in this case not yet be made unambiguously.

TABLE 3

Resulting matrix for the persons with kidney rejection.
Correlation matrix of the 20 selected integral values

|  | value 1 | value 2 | value 3 | value 4 | value 5 | value 6 | value 7 | value 8 | value 9 | value 10 |
|---|---|---|---|---|---|---|---|---|---|---|
| value 1  | 1.00  | 0.75 | 1.87  | 0.24 | 2.17  | 1.84  | 3.38  | 1.08  | 1.59  | 2.28  |
| value 2  | 4.93  | 1.00 | 3.19  | 0.76 | 4.90  | 3.19  | 6.10  | 1.91  | 2.65  | 4.59  |
| value 3  | 1.64  | 0.73 | 1.00  | 0.24 | 2.01  | 1.43  | 2.18  | 0.84  | 1.26  | 1.51  |
| value 4  | 24.90 | 9.68 | 21.22 | 1.00 | 26.98 | 24.13 | 25.89 | 14.99 | 22.00 | 25.59 |
| value 5  | 2.41  | 1.56 | 2.56  | 0.58 | 1.00  | 2.58  | 2.12  | 1.31  | 2.92  | 2.51  |
| value 6  | 2.66  | 1.17 | 2.98  | 0.46 | 3.05  | 1.00  | 2.48  | 1.44  | 2.32  | 5.20  |
| value 7  | 1.37  | 0.68 | 1.43  | 0.27 | 1.46  | 1.00  | 1.00  | 0.76  | 1.70  | 2.07  |
| value 8  | 4.35  | 2.38 | 3.59  | 0.63 | 5.43  | 2.84  | 9.28  | 1.00  | 4.18  | 6.67  |
| value 9  | 1.81  | 0.81 | 1.73  | 0.61 | 2.23  | 1.54  | 1.97  | 1.12  | 1.00  | 2.51  |
| value 10 | 4.78  | 1.37 | 2.74  | 2.21 | 4.96  | 5.45  | 6.76  | 2.30  | 2.69  | 1.00  |
| value 11 | 3.34  | 0.99 | 1.96  | 1.54 | 3.80  | 3.73  | 4.38  | 1.59  | 1.86  | 0.98  |
| value 12 | 8.56  | 2.44 | 4.78  | 3.40 | 9.49  | 10.09 | 11.44 | 3.98  | 4.88  | 2.49  |
| value 13 | 2.05  | 0.80 | 1.41  | 0.12 | 1.51  | 1.23  | 2.62  | 0.86  | 0.88  | 2.90  |
| value 14 | 1.68  | 0.69 | 1.83  | 0.27 | 2.13  | 1.50  | 2.28  | 1.00  | 1.53  | 2.82  |
| value 15 | 4.79  | 1.30 | 2.68  | 1.93 | 5.39  | 5.66  | 6.64  | 2.18  | 2.67  | 1.26  |
| value 16 | 1.66  | 0.99 | 1.72  | 0.41 | 2.25  | 1.55  | 2.28  | 1.06  | 1.84  | 3.05  |
| value 17 | 1.51  | 0.88 | 1.72  | 0.36 | 1.25  | 1.35  | 1.84  | 1.23  | 1.31  | 2.16  |
| value 18 | 1.10  | 0.66 | 1.31  | 0.25 | 0.97  | 1.03  | 1.36  | 0.91  | 0.97  | 1.71  |
| value 19 | 1.27  | 0.90 | 1.74  | 0.20 | 0.82  | 1.46  | 1.48  | 0.86  | 2.10  | 1.69  |
| value 20 | 2.00  | 1.46 | 2.78  | 0.30 | 1.33  | 2.26  | 2.30  | 1.31  | 3.34  | 2.79  |

|  | value 11 | value 12 | value 13 | value 14 | value 15 | value 16 | value 17 | value 18 | value 19 |
|---|---|---|---|---|---|---|---|---|---|
| value 1  | 2.10  | 1.49  | 1.13  | 1.63  | 4.75  | 2.32  | 2.57  | 3.44  | 3.29  |
| value 2  | 4.26  | 1.97  | 4.65  | 2.52  | 11.29 | 5.12  | 7.09  | 11.10 | 11.08 |
| value 3  | 1.71  | 1.00  | 1.59  | 1.71  | 4.31  | 1.91  | 2.68  | 4.14  | 4.88  |
| value 4  | 26.83 | 19.95 | 15.61 | 15.64 | 96.73 | 33.18 | 47.86 | 81.34 | 67.66 |
| value 5  | 3.21  | 2.42  | 5.97  | 2.62  | 11.52 | 2.61  | 1.59  | 2.22  | 2.48  |
| value 6  | 4.33  | 1.84  | 1.60  | 2.03  | 6.77  | 3.89  | 2.91  | 3.77  | 5.15  |
| value 7  | 1.86  | 1.37  | 1.05  | 1.13  | 6.56  | 2.01  | 1.94  | 2.64  | 2.63  |
| value 8  | 7.13  | 3.74  | 3.39  | 3.67  | 28.82 | 3.98  | 7.01  | 9.10  | 9.66  |
| value 9  | 2.30  | 1.14  | 1.94  | 1.78  | 6.55  | 3.02  | 3.19  | 3.85  | 5.30  |
| value 10 | 1.54  | 0.79  | 1.60  | 3.51  | 3.13  | 3.03  | 7.68  | 10.50 | 17.61 |
| value 11 | 1.00  | 0.54  | 1.20  | 2.69  | 4.67  | 2.48  | 6.30  | 7.87  | 12.31 |
| value 12 | 2.40  | 1.00  | 2.86  | 6.64  | 3.06  | 5.78  | 15.03 | 20.65 | 33.26 |
| value 13 | 3.55  | 1.72  | 1.00  | 1.52  | 10.15 | 2.55  | 1.24  | 1.72  | 3.85  |
| value 14 | 2.37  | 1.49  | 1.28  | 1.00  | 7.05  | 2.11  | 3.06  | 4.66  | 3.97  |
| value 15 | 1.19  | 0.52  | 1.89  | 3.62  | 1.00  | 3.10  | 8.68  | 12.26 | 19.02 |
| value 16 | 2.07  | 1.60  | 1.16  | 1.73  | 7.18  | 1.00  | 2.50  | 3.17  | 3.86  |
| value 17 | 2.34  | 1.45  | 2.52  | 1.57  | 6.66  | 3.69  | 1.00  | 1.41  | 2.34  |
| value 18 | 1.85  | 1.13  | 1.86  | 1.18  | 5.19  | 2.74  | 0.78  | 1.00  | 1.75  |

TABLE 3-continued

Resulting matrix for the persons with kidney rejection.
Correlation matrix of the 20 selected integral values

| | | | | | | | | | |
|---|---|---|---|---|---|---|---|---|---|
| value 19 | 2.68 | 1.79 | 2.70 | 1.31 | 8.60 | 2.05 | 0.98 | 1.53 | 1.00 |
| value 20 | 4.11 | 2.70 | 4.31 | 2.08 | 13.25 | 3.27 | 1.76 | 2.56 | 1.91 |

TABLE 4

Choice of meaningful matrix elements on the basis of weighted values.

| USE | value 1 | value 2 | value 3 | value 4 | value 5 | value 6 | value 7 | value 8 | value 9 | value 10 | value 11 | value 12 | value 13 | value 14 | value 15 | value 16 | value 17 | value 18 | value 19 | value 20 |
|---|---|---|---|---|---|---|---|---|---|---|---|---|---|---|---|---|---|---|---|---|
| value 1 | 1.0 | 0.0 | 0.0 | 23.3 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| value 2 | 0.0 | 1.0 | 0.0 | 0.0 | 0.0 | 0.0 | 0.0 | 0.0 | 0.0 | 24.8 | 0.0 | 0.0 | 0.0 | 0.0 | 0.0 | 0.0 | 0.0 | 0.0 | 0.0 | 0.0 |
| value 3 | 0.0 | 0.0 | 1.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| value 4 | 0.0 | 0.0 | 0.0 | 1.0 | 0.0 | 0.0 | 0.0 | 77.4 | 0.0 | 0.0 | 0.0 | 0.0 | 0.0 | 0.0 | 0.0 | 0.0 | 0.0 | 0.0 | 0.0 | 0.0 |
| value 5 | 0.0 | 0.0 | 0.0 | 0.0 | 1.0 | 0.0 | 0.0 | 0.0 | 0.0 | 0.0 | 0.0 | 0.0 | 23.4 | 0.0 | 0.0 | 0.0 | 0.0 | 0.0 | 0.0 | 0.0 |
| value 6 | 7.5 | 0.0 | 0.0 | 0.0 | 0.0 | 1.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| value 7 | 0.0 | 0.0 | 0.0 | 0.0 | 0.0 | 52.3 | 1.0 | 0.0 | 0.0 | 0.0 | 0.0 | 0.0 | 0.0 | 0.0 | 0.0 | 0.0 | 0.0 | 0.0 | 0.0 | 0.0 |
| value 8 | 0.0 | 0.0 | 0.0 | 0.0 | 0.0 | 0.0 | 11.9 | 1.0 | 0.0 | 0.0 | 0.0 | 0.0 | 0.0 | 56.7 | 0.0 | 0.0 | 23.4 | 0.0 | 0.0 | 0.0 |
| value 9 | 0.0 | 0.0 | 0.0 | 0.0 | 0.0 | 0.0 | 0.0 | 0.0 | 1.0 | 0.0 | 0.0 | 70.4 | 0.0 | 0.0 | 0.0 | 0.0 | 0.0 | 15.6 | 0.0 | 0.0 |
| value 10 | 0.0 | 0.0 | 0.0 | 0.0 | 0.0 | 0.0 | 0.0 | 0.0 | 0.0 | 1.0 | 0.0 | 0.0 | 0.0 | 0.0 | 0.0 | 0.0 | 0.0 | 0.0 | 0.0 | 0.0 |
| value 11 | 11.3 | 0.0 | 0.0 | 2.0 | 0.0 | 2.4 | 0.0 | 0.0 | 0.0 | 0.0 | 1.0 | 0.0 | 0.0 | 0.0 | 0.0 | 0.0 | 0.0 | 0.0 | 0.0 | 0.0 |
| value 12 | 0.0 | 0.0 | 0.0 | 7.8 | 5.2 | 14.2 | 0.0 | 0.0 | 0.0 | 0.0 | 0.0 | 1.0 | 0.0 | 0.0 | 0.0 | 0.0 | 0.0 | 0.0 | 0.0 | 0.0 |
| value 13 | 0.0 | 0.0 | 0.0 | 25.9 | 0.0 | 0.0 | 0.0 | 0.0 | 0.0 | 0.0 | 0.0 | 0.0 | 1.0 | 0.0 | 0.0 | 0.0 | 0.0 | 0.0 | 0.0 | 0.0 |
| value 14 | 0.0 | 0.0 | 0.0 | 0.0 | 0.0 | 0.0 | 0.0 | 0.0 | 0.0 | 0.0 | 0.0 | 0.0 | 0.0 | 1.0 | 0.0 | 0.0 | 0.0 | 0.0 | 0.0 | 0.0 |
| value 15 | 0.0 | 0.0 | 0.0 | 0.0 | 0.0 | 0.0 | 0.0 | 0.0 | 0.0 | 0.0 | 0.0 | 0.0 | 0.0 | 0.0 | 1.0 | 0.0 | 0.0 | 0.0 | 0.0 | 0.0 |
| value 16 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 1.0 | 0.0 | 0.0 | 0.0 | 0.0 |
| value 17 | 0.0 | 79.1 | 17.5 | 0.0 | 0.0 | 0.0 | 0.0 | 0.0 | 0.0 | 0.0 | 0.0 | 0.0 | 0.0 | 0.0 | 0.0 | 0.0 | 1.0 | 0.0 | 0.0 | 0.0 |
| value 18 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 1.0 | 0.0 | 0.0 |
| value 19 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 1.0 | 0.0 |
| value 20 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 1.0 |

TABLE 5

Assignment of substances to the peculiar signals.

| Number | Signal position [ppm] | Assignment (substance) |
|---|---|---|
| 1 | 1.174 | methyl malonate (?) |
| 2 | 1.310 | lactate |
| 3 | 2.132 | methyl succinate |
| 4 | 2.198 | p-cresol |
| 5 | 2.330 | 3-hydroxy isovalerate |
| 6 | 2.513 | citrate |
| 7 | 2.767 | methyl guanidine |
| 8 | 3.096 | malonate |
| 9 | 3.105 | malonate |
| 10 | 3.222 | taurine |
| 11 | 3.378 | methyl guanidine |
| 12 | 3.394 | taurine |
| 13 | 3.779 | PAG |
| 14 | 4.386 | trigonelline (?) |
| 15 | 5.223 | α-glucose |
| 16 | 5.601 | acetyl carnitine |
| 17 | 7.335 | PAG/phenyl acetate |
| 18 | 7.396 | PAG/phenyl acetate |
| 19 | 7.551 | hippurate |
| 20 | 7.828 | hippurate |

Furthermore, with the help of the generated correlation matrix it was determined between which of the assigned substances significant correlations exist. These correlations are depicted in FIG. 24.

Figure 7:
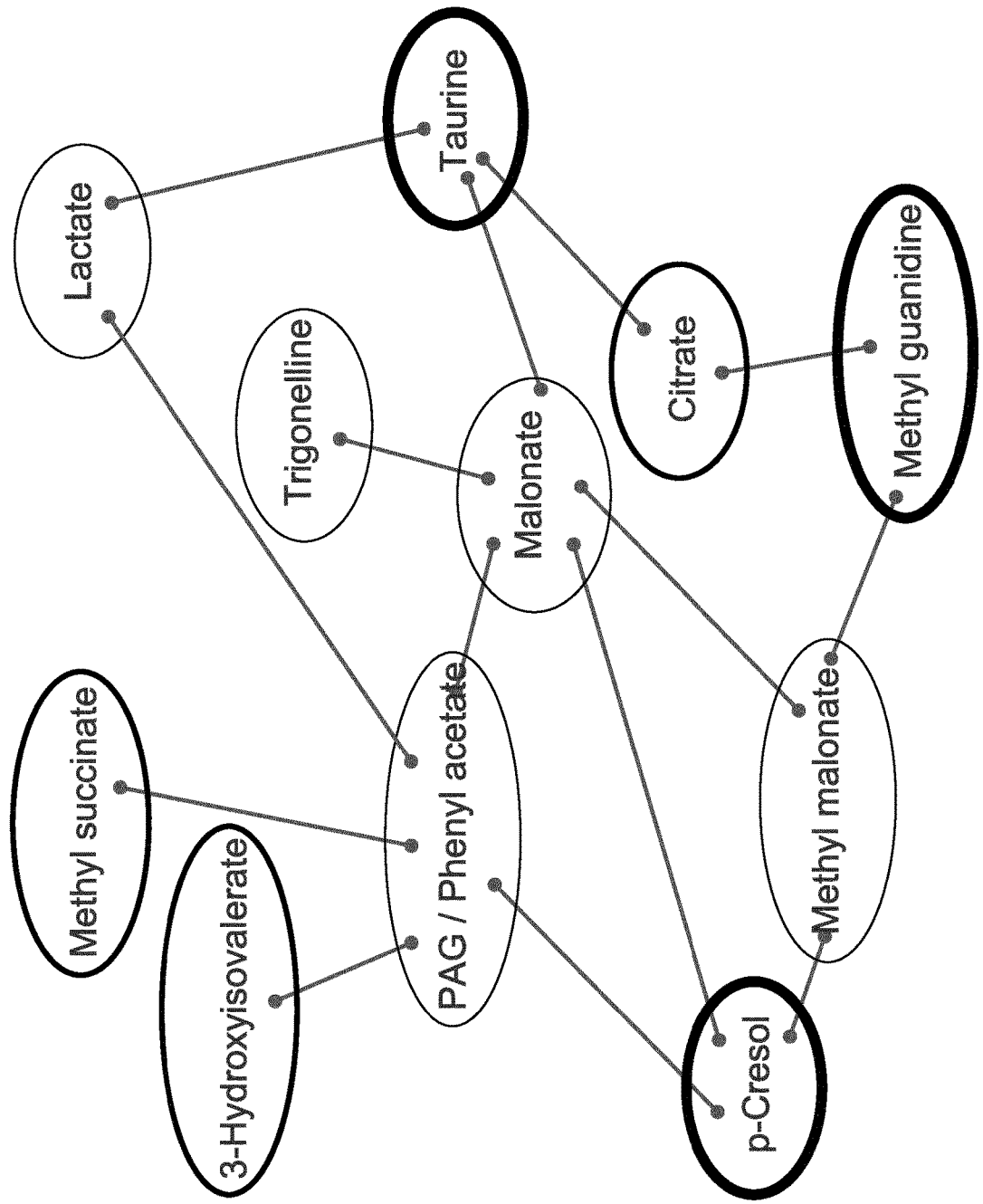
FIG. 7 shows a schematic depiction of a metabolic network of substances playing a role in kidney rejection assessment.

This assignment is also depicted in FIG. 7 in form of a metabolic network. By the effected assignment and the determination of significant correlations of the assigned substances to each other it is possible to determine which of the substances are in interaction to each other within the metabolic pathways. This is an interesting additional aspect which can be co-observed within the framework of the present signature generating.

In order to not only assign a signature to each of the examined persons, but to determine with the aid of the according signature also whether the person is to be assigned to the group of kidney rejecters or the kidney non-rejecters, the according signature was compared with comparative signatures of the respective groups. In this manner, it can be determined whether the network of relative substance concentrations, this means the signature, resembles rather the class of kidney rejecters or rather the class of kidney non-rejecters.

In order to determine here a similarity between the respective signatures, the signature of the sample to be evaluated was compared in each matrix element with the according matrix element of the signature of the comparative group. Thereby, according differences were calculated and weighted. The similarity of the sample to be evaluated to the respective comparative group finally results as sum over the weighted deviations of all matrix elements.

Figure 8:
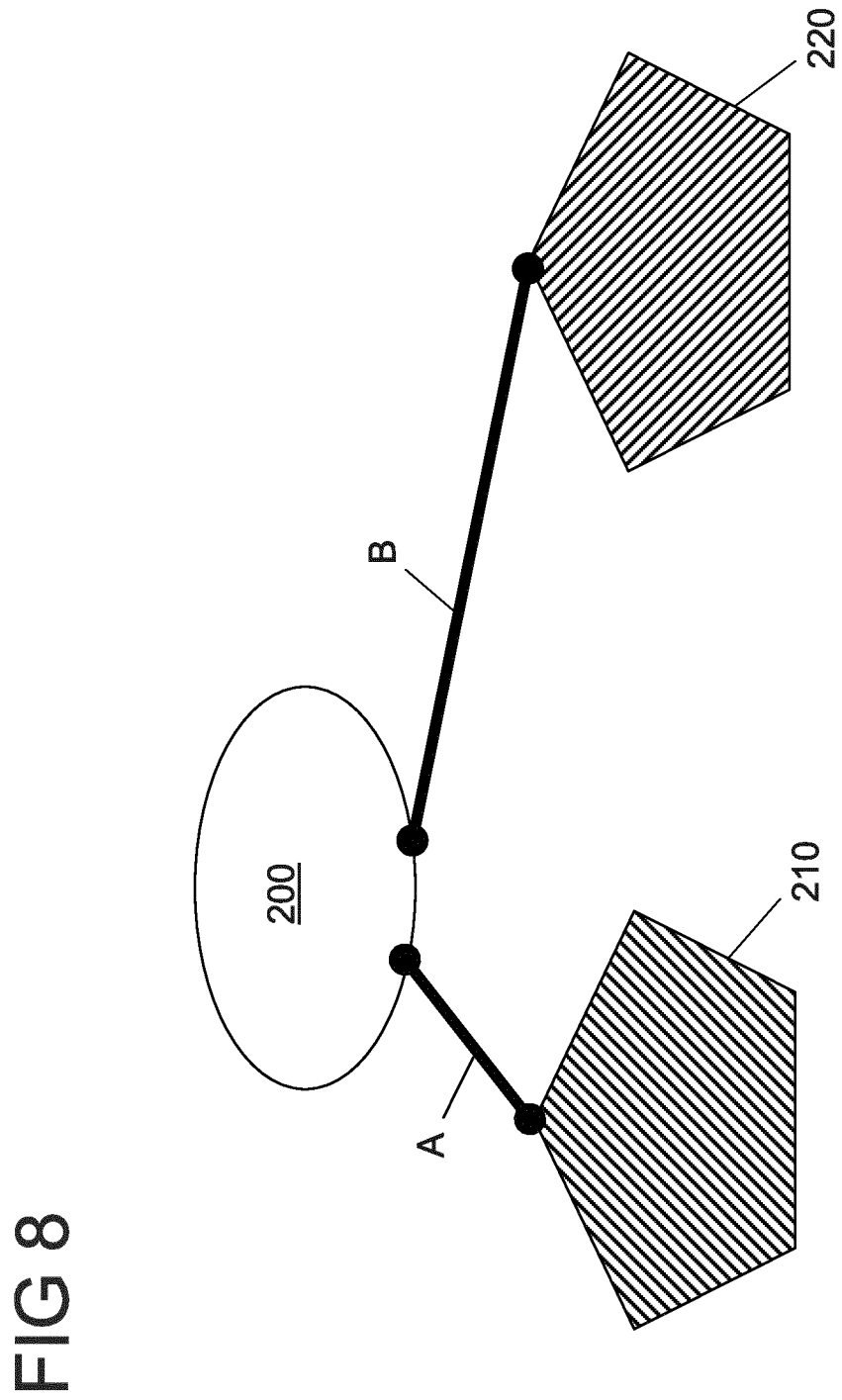
FIG. 8 shows a schematic depiction of the classification of a measured signature by using already existing signatures.

If this measured NMR signature is now compared to a comparative signature of kidney rejecters and a comparative signature of kidney non-rejecters, a distance between the measured NMR signature and the signature of the kidney rejecters as well as the signature of the kidney non-rejecters results from the applied similarity criterion (namely the weighted sum of all deviations between the measurement to be evaluated and the comparative signature). This is schematically depicted in FIG. 8. Here, on the one hand the measured NMR signature 200 can be seen which is located in a distance A from the signature 210 of the group of the kidney non-rejecters and in a distance B from the signature 220 of the group of kidney rejecters. Presently, the distance A is smaller than the distance B. From both values, the score can be calculated via the equation:

score=((distance $A$)/(distance $B$))*adjustment

If this score is lower than the value of 1, the measured NMR signature 200 is to be assigned rather to the signature 210 of the groups of kidney non-rejecters. If the value of the score is higher than 1, the measured NMR signature 200 is rather to be assigned to the signature 220 of the groups of kidney non-rejecters.

In this manner, of course not only a single measured NMR signature 200 can be assigned to an according comparative group but also a plurality of measured NMR signatures. This is exemplarily depicted in FIG. 9, wherein the same numeral reference 200 was assigned to all measured NMR signatures. The measured NMR signatures depicted in FIG. 9 exhibit in each case a distance A which is smaller than the according distance B. This means that the measured NMR signatures 200 depicted in FIG. 9 are in each case rather to be assigned to the signature 210 of the kidney non-rejecters.

Figure 9:
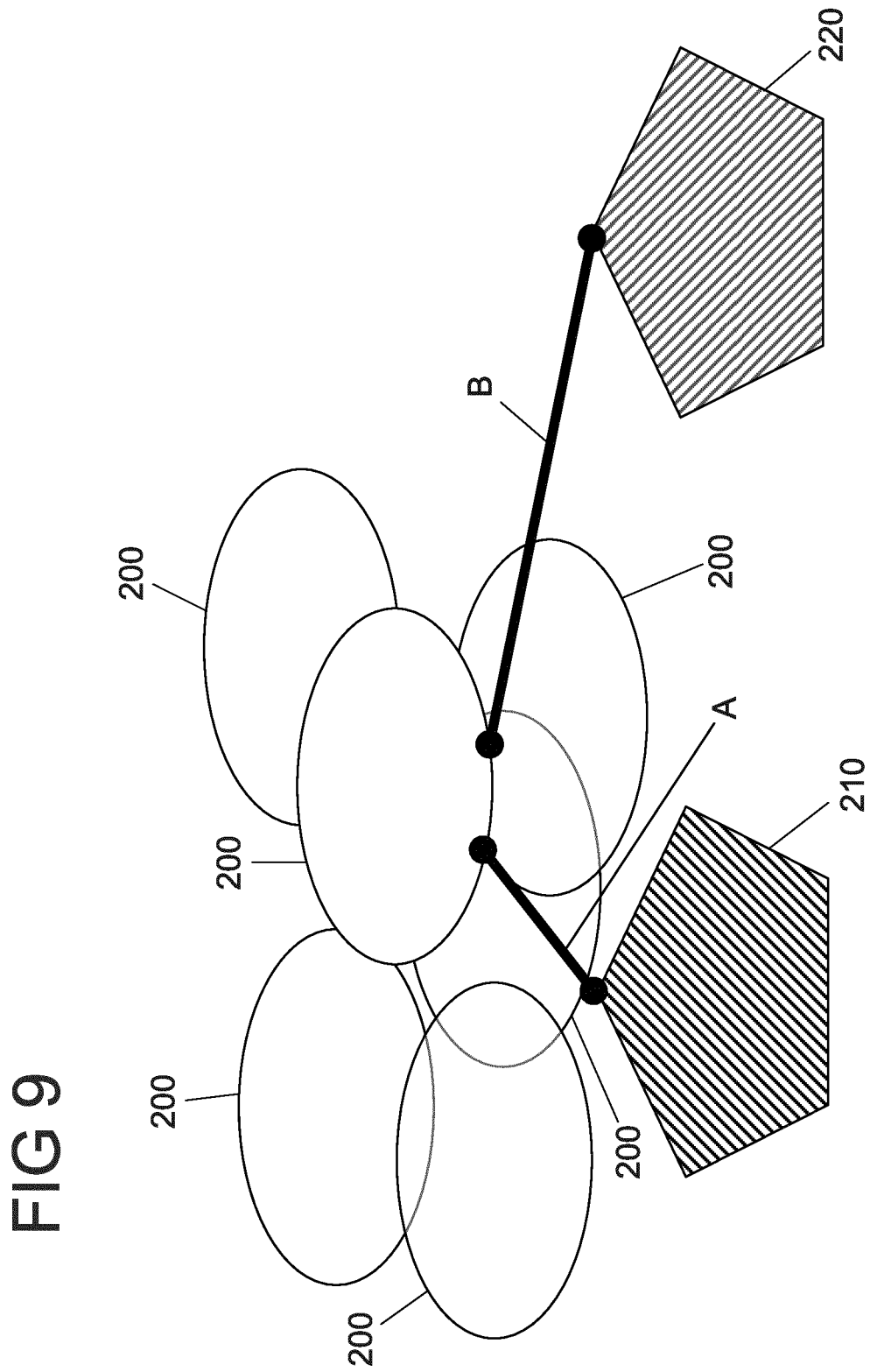
FIG. 9 shows a schematic depiction of the classification of different measured signatures by using already existing signatures.
Figure 10:
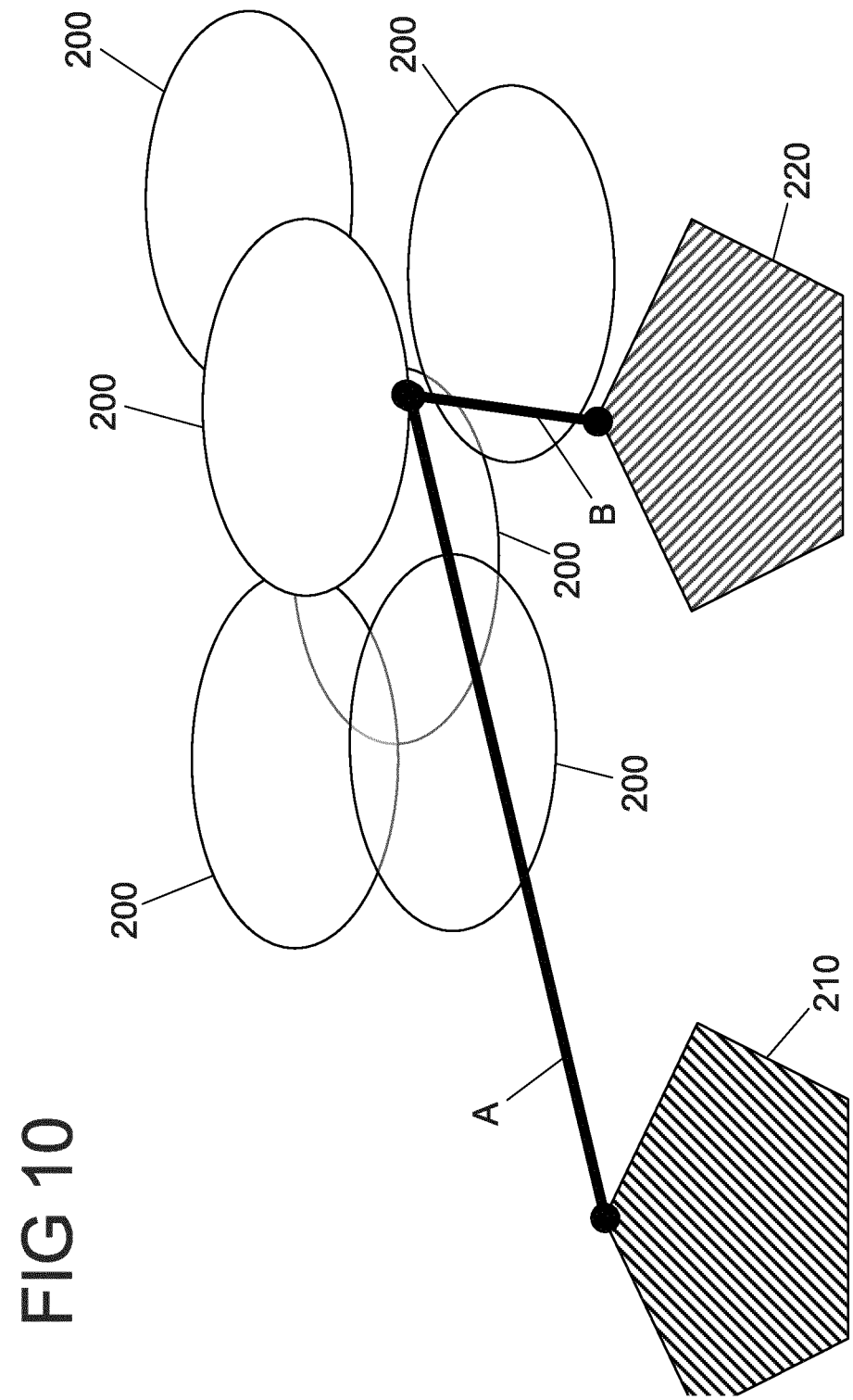
FIG. 10 shows a further schematic depiction of the classification of different measured signatures by using already existing signatures.

In FIG. 10, a picture comparable to FIG. 9 is depicted, wherein here, however, the NMR signatures 200 measured in each case are rather to be assigned to the group of kidney rejecters than to the group of kidney non-rejecters. FIGS. 9 and 10 thereby serve only for illustration purposes as to how the relation between the measured NMR signatures 200 and the signature 220 of the kidney rejecters and signature 210 of the kidney-non rejecters being already present as reference data sets is to be understood.

With the aid of the calculated score for a measured NMR signature 200, it is possible to determine with which probability a person undergoing kidney transplantation will reject the transplanted kidney.

Figure 11:
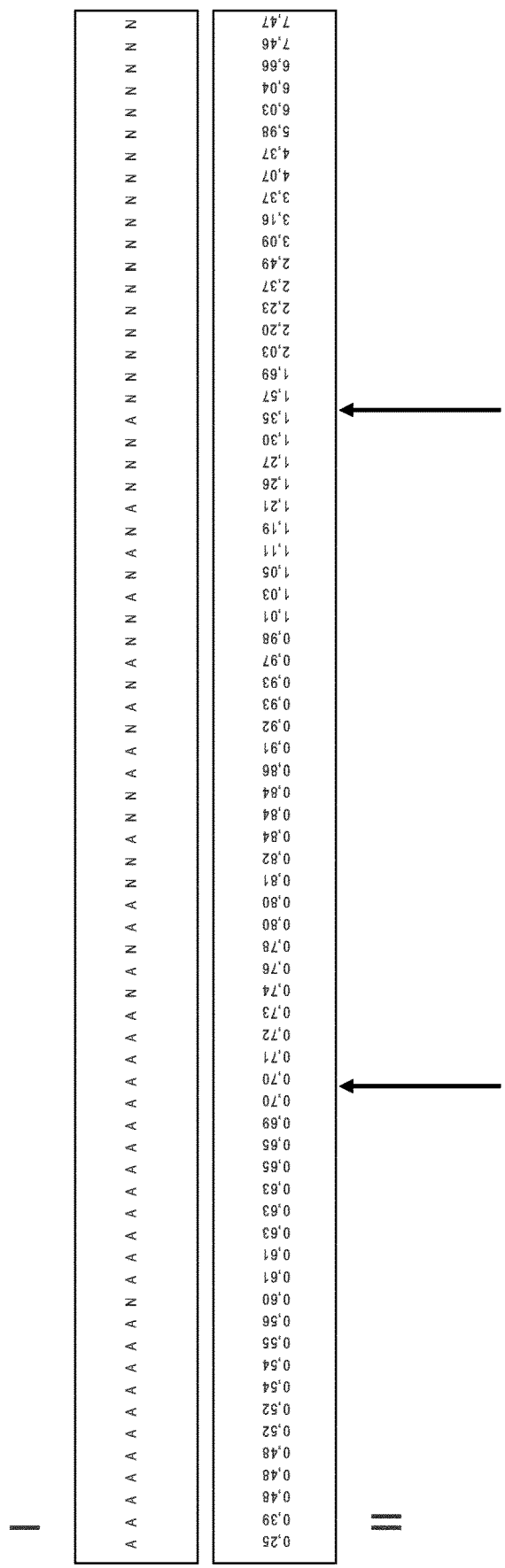
FIG. 11 shows a schematic comparison of clinical diagnostic findings and a prognosis for a clinical picture generated by NMR signatures.

In FIG. 11, a comparison with clinical findings is depicted for validating the present characterization method by a characterizing signature. Thus, the clinical findings of different patients after kidney transplantation is depicted in FIG. 11 in the upper box denominated with I by the letters "A" and "N". Thereby, "A" denotes a kidney rejection after kidney transplantation and "N" a kidney non-rejection after transplantation.

In the box denoted with II and depicted in FIG. 11 in the lower part, the scores of the NMR prognosis on the basis of the characterizing signature is depicted. As already explained, a score of lower than 1 denotes a kidney rejection, and a score of higher than 1 a kidney non-rejection after transplantation. Thereby, the further remote from 1 the score is, the higher is the probability that the behaviour after transplantation predicted by NMR prognosis corresponds to the factual behaviour of the according patient. Considering only the scores which are smaller than 0.7 or higher than 1.4 (marked by arrows in each case), the kidney rejecters can be correctly predicted to 95% by the method of NMR signatures. Under these prerequisites, kidney non-rejecters can even be correctly predicted to 100%.

The present method for using a characterizing signature can thus be excellently used for the prediction of the behaviours of a patient on upcoming kidney transplantation. However, as explained above, the present method is not limited to such predictions in the area of kidney transplantations, but can find a manifold field of application.

Now, FIGS. 12 to 17 will be explained in connection to a second exemplary embodiment.

Second Exemplary Embodiment: Coffee Type Identification

A "Nespresso" coffee capsule containing ca. 5 g coffee powder was inserted into a "Nespresso" coffee machine. The coffee powder was extracted by ca. 120 ml hot water according to the standard extraction proceedings performed by the coffee machine. Ca. 118 ml liquid coffee extract were obtained. 50 µl sodium phosphate buffer and 25 µl NMR standard (consisting of 2 mmol/l trimethylsilyl propionate [TSP] in $D_2O$) were added to 425 µl of the coffee extract. This mixture was then transferred into a 5-mm NMR sample tube for the subsequent NMR measurement.

An NMR spectrometer of the type Advance II+600 having a TXI sample head was used for NMR measurement. The height of the sample tube in the spinner was 20 mm and the adjusted actual temperature was 298 K. The maximum storage time of the sample at room/measuring temperature was four hours. The measurement was started when a sufficient temperature equilibration was present; this was the case if the temperature fluctuation of the sample was within ±0.2 K of the nominal temperature.

For the actual NMR measurement, a parameter set was used which is depicted in subsequent table 6. By an NMR measurement with the according parameters an automatically processed spectrum was obtained for each sample. A phase correction, a baseline correction and a referencing were carried out during the automatic processing.

TABLE 6

Overview over the parameters used during the NMR measurement

| Acquisition (variable) | Acquisition (variable) | Processing (variable) |
|---|---|---|
| p1~10 µs | PI1: 0 dB | SI: 64 k |
| pl9: 65 dB | TD: 32 k | WDW: EM |
| o1: 2852 Hz | DS: 4 | LB[Hz]: 0.3 |
| | | PHC1: 0 |
| | | PH_mod: pk |

This coffee extraction and NMR measurement was repeated for different kinds or types of coffee, each contained in a "Nespresso" capsule. These coffee types differed in their caffeine content, in their coffee composition and in their roasting degree.

Figure 12:
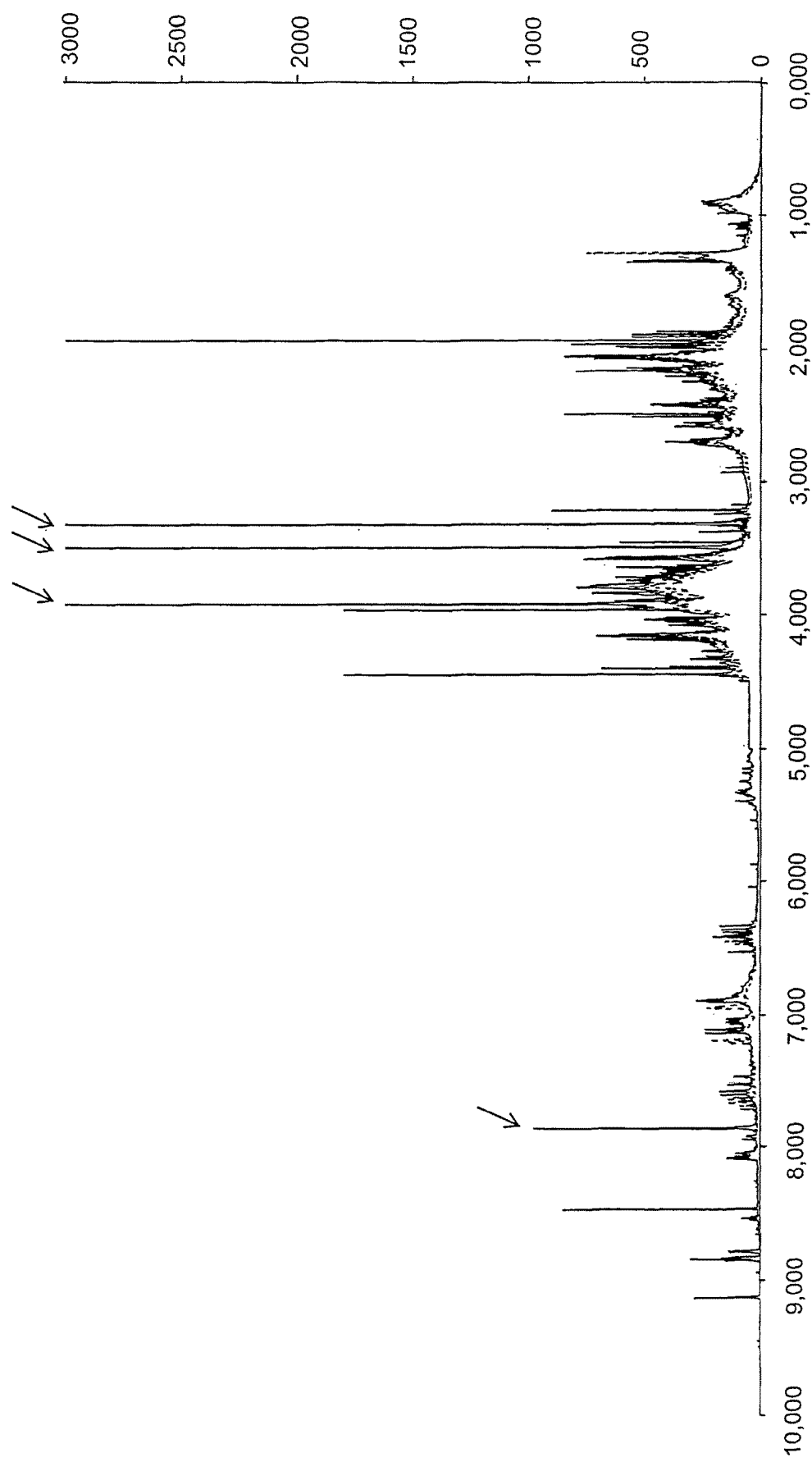
FIG. 12 shows NMR spectra of caffeine-containing coffee and decaffeinated coffee.

Exemplary processed NMR spectra of a caffeine-containing coffee (continuous line) and a decaffeinated coffee (dashed line) are depicted in FIG. 12. The intensity on the y-axis is depicted in arbitrary units over the chemical shift in ppm on the x-axis. Signals lying in the range of resonances of water are suppressed. Peaks that could only be observed in the NMR spectrum of caffeine-containing coffee indicate peaks being caused by caffeine. These peaks are marked with an arrow.

Figure 13:
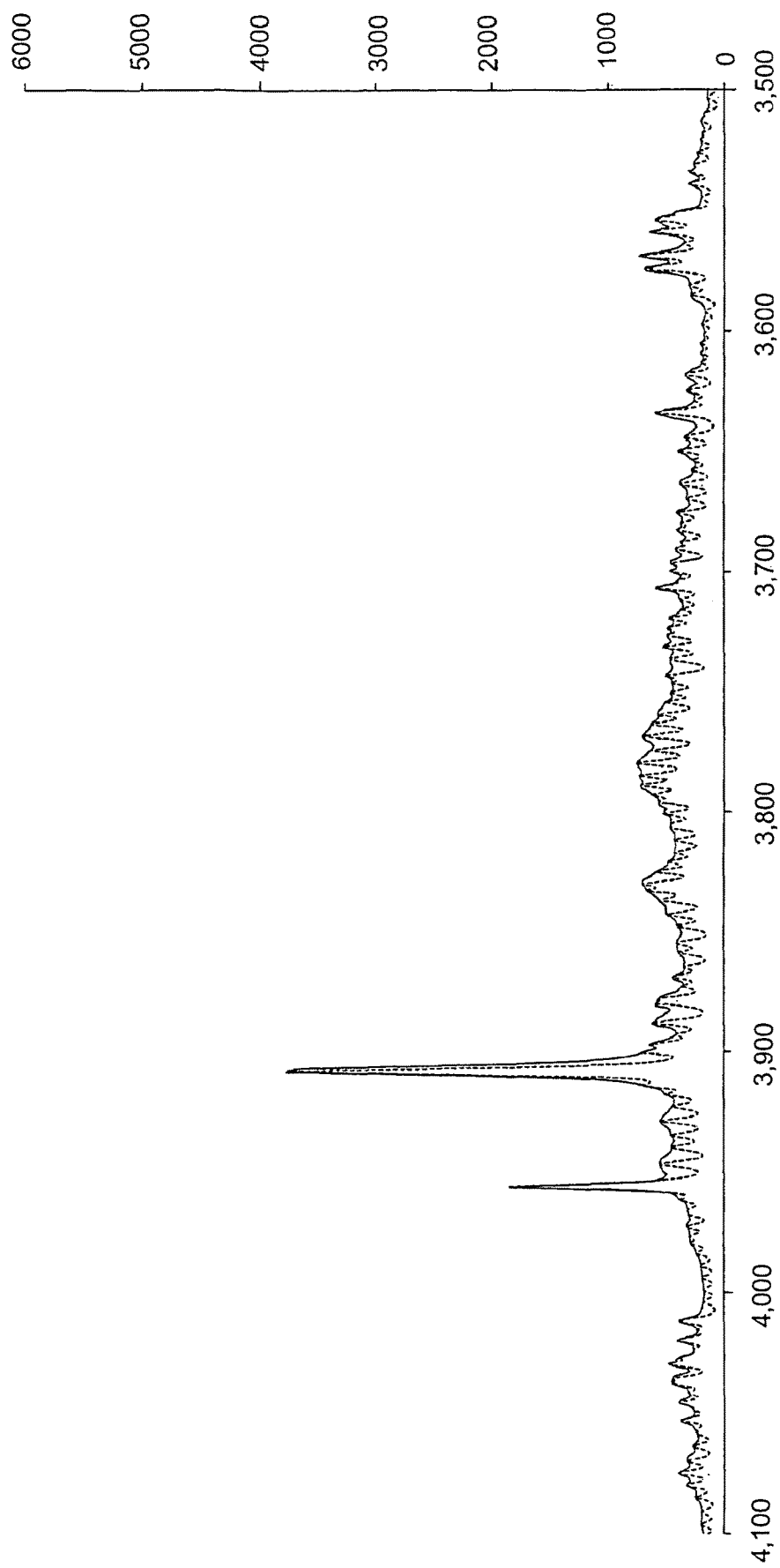
FIG. 13 shows a measured NMR spectrum of coffee and a synthetic NMR spectrum of coffee.

Subsequently, the lines of the individual NMR spectra were separated, i.e. the measured spectrum was transformed to a synthetic spectrum consisting of a plurality of sharp peaks having a defined area. FIG. 13 depicts a measured spectrum (continuous line) and a synthetic spectrum (dashed line). The intensity on the y-axis is depicted in arbitrary units over the chemical shift in ppm on the x-axis.

Figure 14:
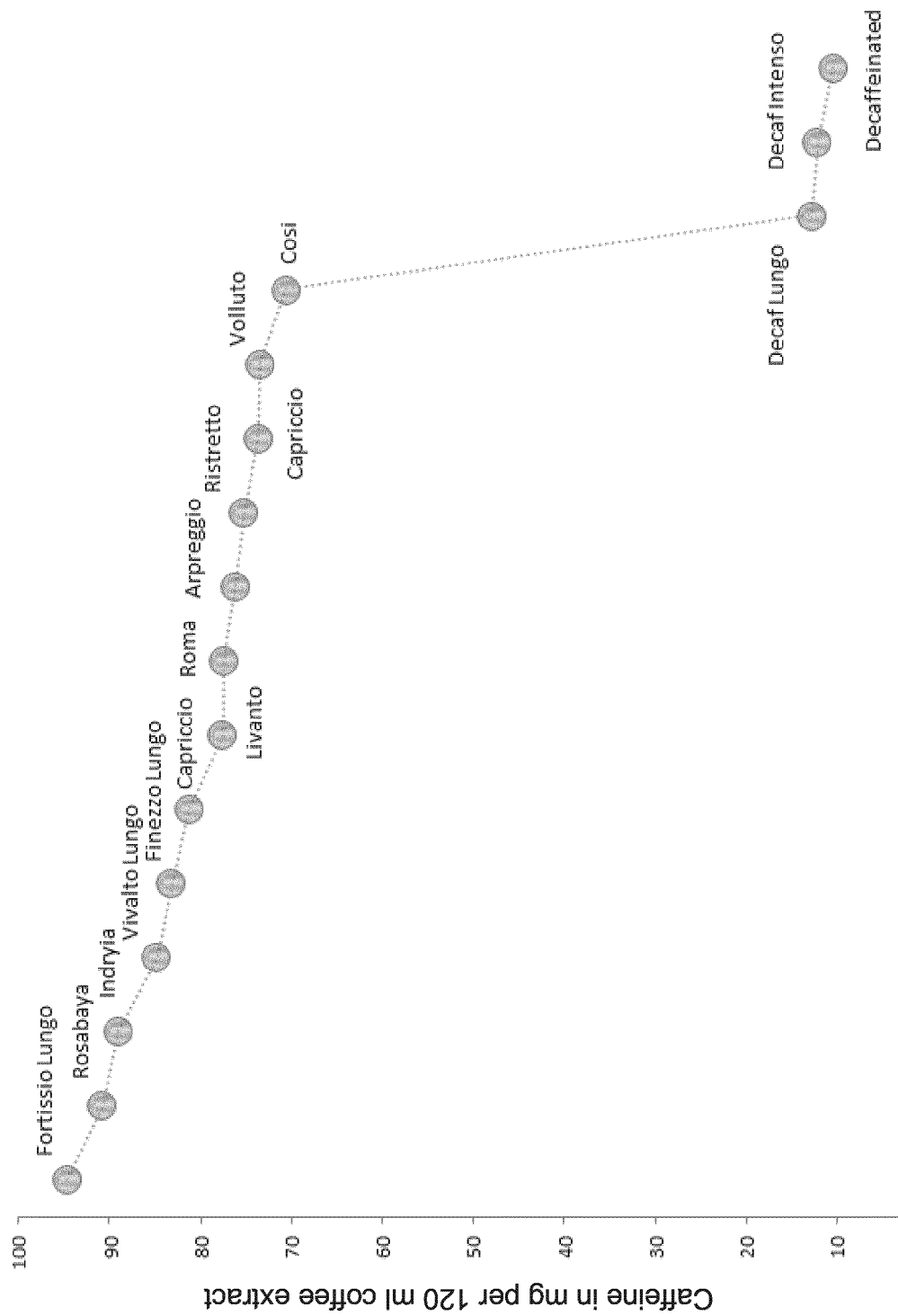
FIG. 14 shows a graphic correlation of different coffee types to their caffeine content, FIG. 15 schematically depicts a method of information coarsening, FIG. 16 schematically depicts a separation of strongly roasted coffees from weakly roasted coffees based on a learned separation rule.

By integrating the area of the peaks caused by caffeine and standardizing it by the area of the peak caused by the NMR standard TSP, a quantification of the caffeine being present in the respective samples was possible. Thus, all measured coffee samples were analyzed with respect to their caffeine content. The result is depicted in FIG. 14. The names depicted in FIG. 14 indicate different types of coffee available for the "Nespresso" system.

Obviously, the caffeine content in the decaffeinated coffee types was significantly lower than that of the non-decaffeinated coffee types. In the latter, "Fortissimo Lungo" contained the highest amount of caffeine, whereas "Cosi" was the coffee having the lowest amount in caffeine of the tested non-decaffeinated coffees.

Besides the caffeine content, different coffees can be best distinguished on the basis of the coffee beans used for the distinct coffee and the degree of roasting. Roasting of the coffee has many small (but no quantitative significant) effects. Nonetheless, the overall chemical composition of the coffee is affected by roasting, resulting in sensory distinctions of differently roasted coffees. In order to classify a coffee as strongly roasted coffee or weakly roasted coffee, a characterizing signature of the coffee extracts was generated.

In doing so, firstly two groups were built on the basis of information provided by the coffee manufacturer on the roasting degree. The coffee types "Ristretto", "Arpeggio", "Fortissio Lungo" and "Decaffeinato Intenso" formed the group "strongly roasted". The coffee types "Finezzo Lungo", "Volluto", "Decaffeinato", "Cosi", "Cappricio" and "Roma" formed the group "weakly roasted".

Figure 15:
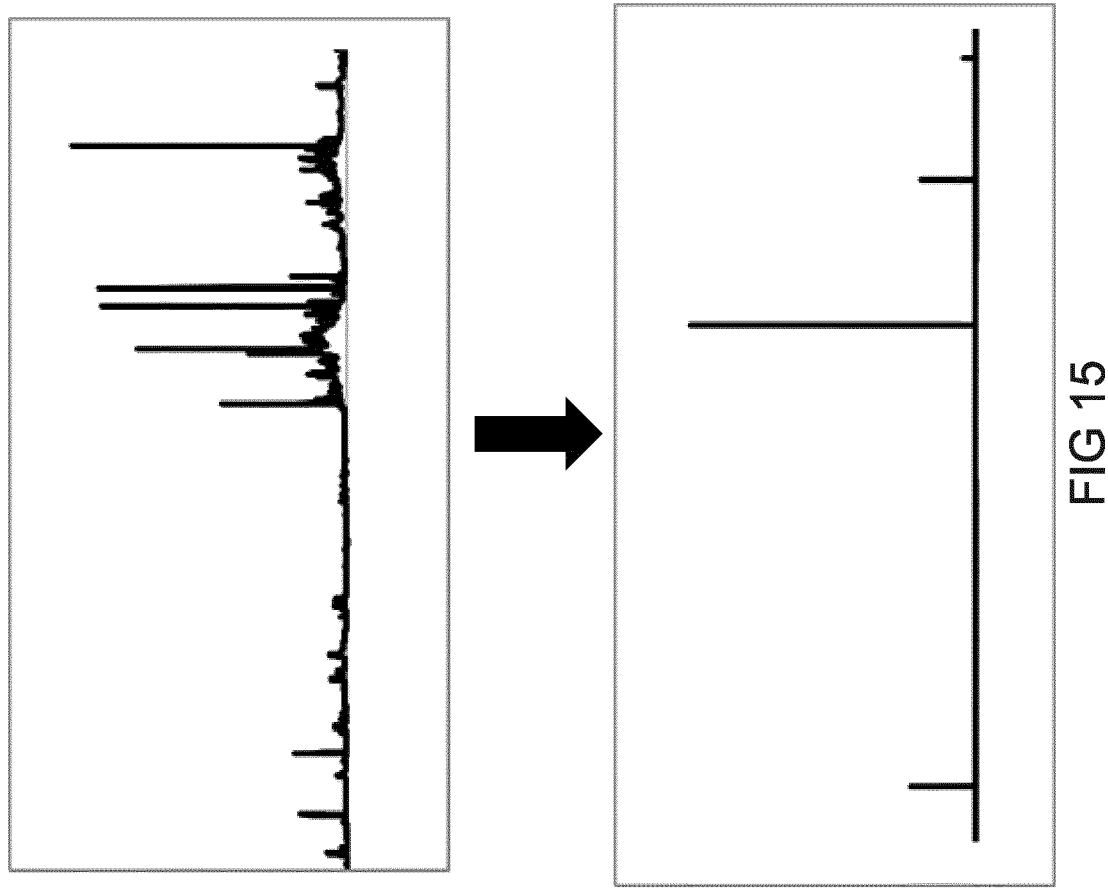

Now, an intelligent information coarsening took place. In doing so, the best separated lines were chosen to reduce the information of the synthetic spectrum to a small group of very well separated lines. Thereby, also very small peaks were considered as long as they could be well separated from their neighbouring peaks. FIG. 15 schematically depicts the information coarsening. In the upper panel of FIG. 15, a synthetic spectrum is depicted. In the lower panel, a coarsened spectrum consisting only of the best separable lines of this synthetic spectrum are shown. In other words, the resulting lines are those lines of the whole spectrum that are as selective as possible.

Figure 16:
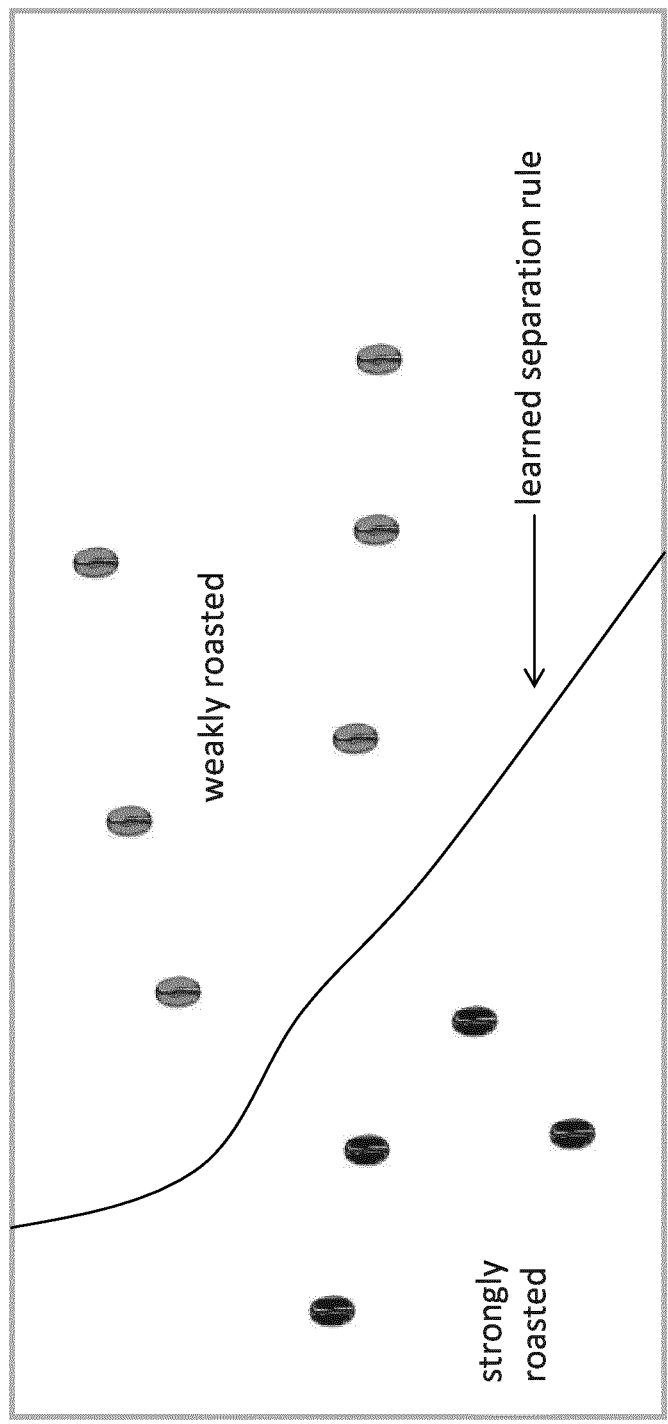

Based on the coarsened spectrum and the remaining, selective lines, the groups "strongly roasted" and "weakly roasted" can be well separated from each other. This is depicted in FIG. 16. Use of only the best separated lines out of the whole spectrum prevents from underfitting or overfitting the separation. Thus, the choice of the best suited peaks results in a "learned" separation rule on the basis of which a distinction between the groups of strongly roasted and weakly roasted coffees can be made very well.

It is possible to not use all of the lines being present in the coarsened spectrum but only a subset thereof. This can be done manually by visually selecting meaningful peaks of average spectra. However, it can be also done automatically by storing all peaks exceeding a threshold value and differing from the peaks observed in the respective other group. Instantly, such an automatic choice was done. This choice was further reduced by keeping only a single peak out of a group of peaks belonging together. Additionally, non-predictive peaks were removed. Finally, the resulting subset of peaks formed the basis for the separation rule and for generating a characterizing signature. Since the preparatory work was aimed to select only the most selective peaks, a selective characterizing coffee signature could be obtained on the basis of these peaks.

The following table 6 shows a set of 6 selective peaks used for generating a coffee signature.

TABLE 6

Selective peaks used for generating a coffee signature.

| Peak no. | Signal position [ppm] | Position of highly correlated peak [ppm] |
|---|---|---|
| 1 | 1.281 | 1.303 |
| 2 | 2.482 | 4.176; 2.409 |
| 3 | 3.554 | 4.154; 1.983; 1.901 |
| 4 | 3.955 | none identified |
| 5 | 5.245 | none identified |
| 6 | 9.127 | 8.838; 4.44 |

For scientific interest, causative substances were assigned to the chosen selective peaks. This assignment is indicated in the following table 7.

TABLE 7

Assignment of causative substances to the selective peaks shown in table 6.

| Peak no. | Signal position [ppm] | Assignment (substance) |
|---|---|---|
| 1 | 1.281 | triglycerides |
| 2 | 2.482 | ? |
| 3 | 3.554 | quinic acid |
| 4 | 3.955 | glycolic acid |
| 5 | 5.245 | ? |
| 6 | 9.127 | trigonelline |

A "?" in table 7 indicates that no causative substance could be identified so that no assignment was yet possible.

As a control, it was looked whether the identified substances would make sense for forming the basis of the coffee signature.

Figure 17:
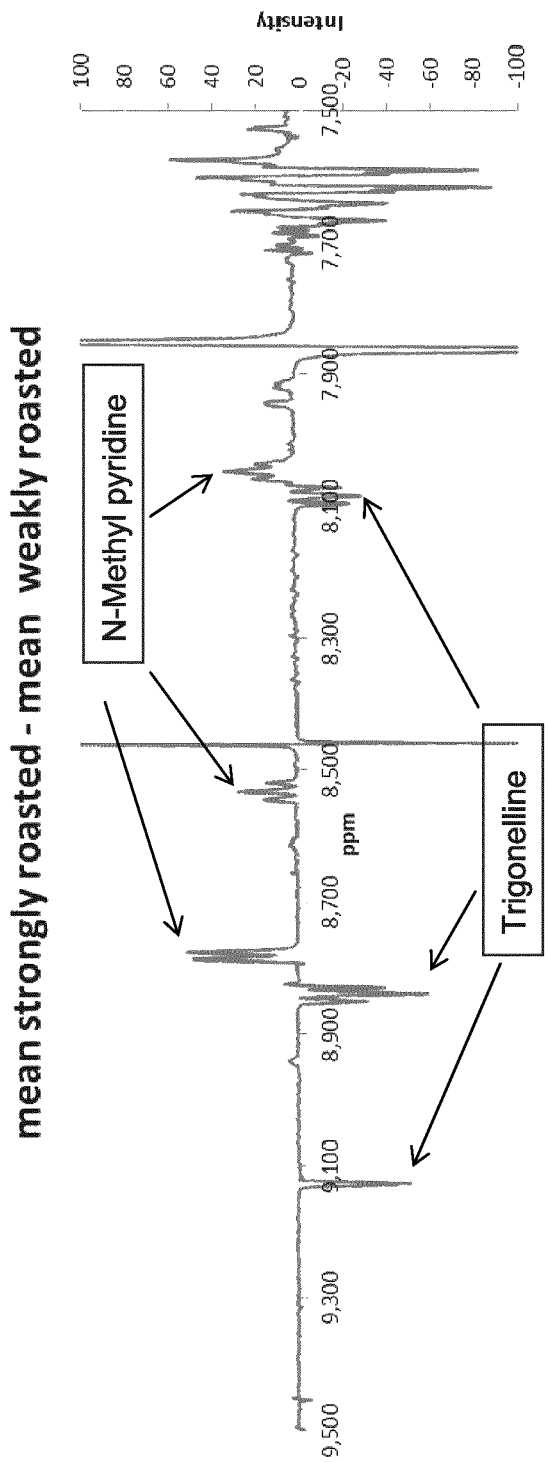
FIG. 17 shows a difference spectrum between the average spectrum of strongly roasted coffees and the average spectrum of weakly roasted coffees.

Trigonelline (1-methylpyridinium-3-carboxylate) is present in coffee in an amount of ca. 0.6%. 50% of the trigonelline is decomposed by roasting the coffee. Decomposition leads to formation of N-methyl pyridine. FIG. 17 shows a difference spectrum between the average spectrum of strongly roasted coffees and the average spectrum of weakly roasted coffees. Substances being present in the group of weakly roasted coffees but not (or to a lower extent) in the group of strongly roasted coffees appear as negative difference peaks. Substances being present in the group of strongly roasted coffees but not (or to a lower extent) in the group of weakly roasted coffees appear as positive difference peaks.

It can be clearly seen from FIG. 17 that trigonelline is present in weakly roasted coffee in a significantly higher amount than in strongly roasted coffee, whereas N-methyl pyridine (the decomposition product of trigonelline) is present in strongly roasted coffee in a significantly higher amount than in weakly roasted coffee.

Thus, the choice of the peak at 9.127 ppm, to which trigonelline was assigned as causative substance, for use of generating a coffee signature appears to be very sensible.

Amongst other acids, quinic acid represents one of the most prominent substances for the total acid content in green coffee. During roasting quinic acid progressively increases as the level of chlorogenic acid decreases. It is assumed that formation of quinic acid during roasting results from the cleavage of chlorogenic acid. In other words, the content of quinic acid in the coffee is strongly interrelated with the degree of roasting. Thus, also the peak at 3.554 ppm caused by quinic acid appears to be a sensible choice for generating a characterizing signature for the coffee.

Without going into details, it could also be established on a scientific basis that triglycerides and glycolic acid are affected by the roasting process. Thus, the choice of the peaks at 1.281 ppm and 3.955 ppm for generating a signature makes also sense.

For generating the signature, a 6×6 correlation matrix was drawn up as described above for each single measured spectrum. This matrix was filled with the values of the quotients between two values (i.e. peak areas) of the analyzed spectrum in each case. Subsequently, meaningful matrix elements were chosen (cf. table 4 and the according description for the general method). These meaningful matrix elements made up the characterizing signature.

Based on a first summed matrix for all coffees pre-grouped into the group of strongly roasted coffees and on a second summed matrix for all coffees grouped into the group of weakly roasted coffees, one signature for strongly roasted coffee and one signature for weakly roasted coffee was generated.

Subsequently, further coffees were extracted, measured and analyzed in an analogous way. Based on the generated signatures of those further coffees and on the already existing signatures for weakly roasted and for strongly roasted coffee, these coffees were grouped in the group of weakly or strongly roasted coffee, respectively. Thereby, all blindly measured coffees could be grouped into the correct group. This was proven by comparing the signature-based indication of the roasting degree with the roasting degree indicated by the coffee manufacturer.

Figure 18:
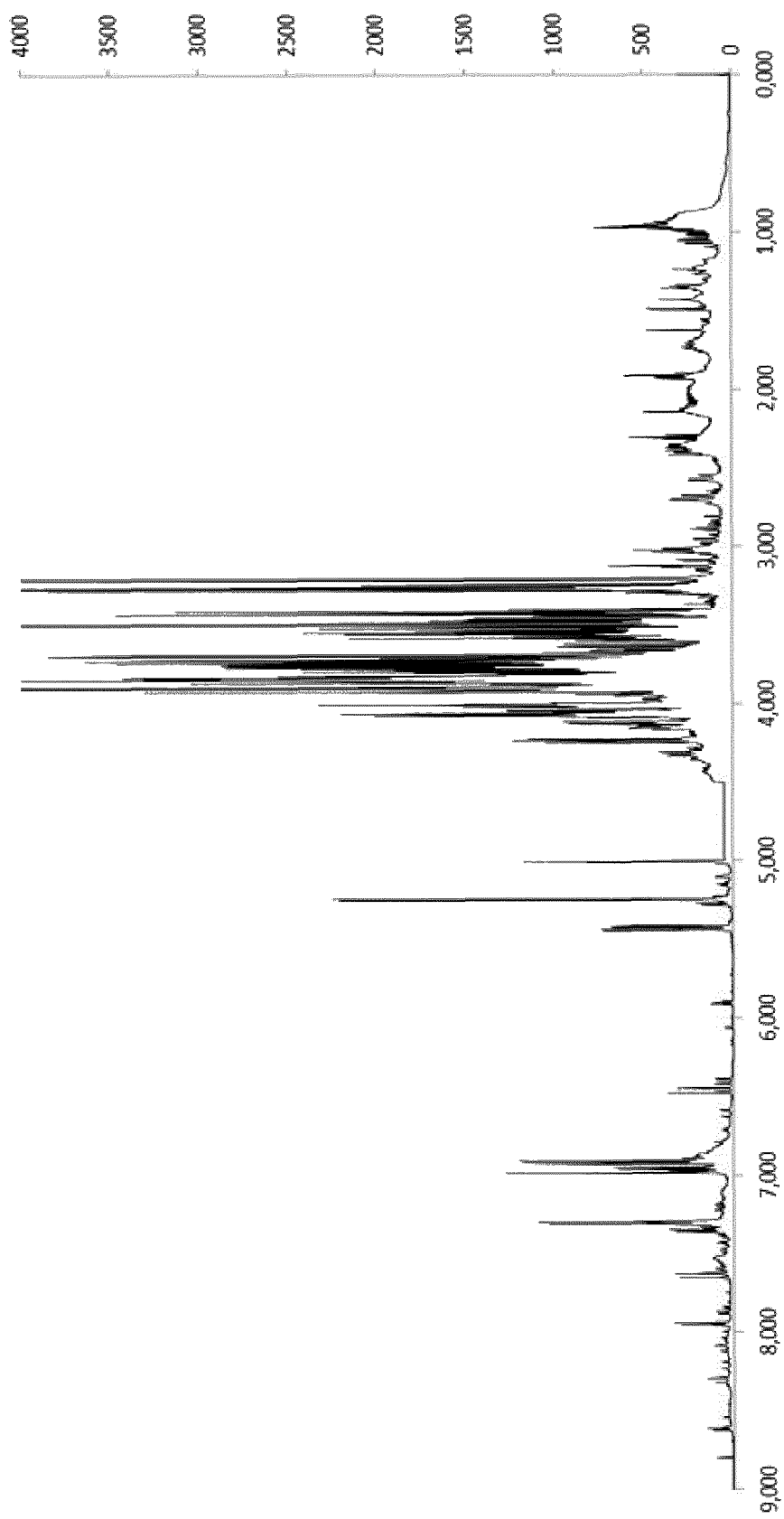
FIG. 18 shows an NMR spectrum of mustard seed extract.

Now, FIGS. 18 and 19 will be explained in connection to a third exemplary embodiment.

Third Exemplary Embodiment: Identification of Mustard Varieties

Mustard seeds contain hundreds of compounds. The ratio of these compounds is determined by growth conditions (environmental influence) and the belonging to a certain variety (genetic influence). A small part of a very complex metabolism network is suited to determine the belonging of a mustard seed to a certain variety.

The inventors were able to show that 50 features of the complex metabolism network are suited for an according classification (i.e. a clarification of the respective variety).

Mustard seeds to be analyzed were chosen by hand to exclude the possibility of contamination of the sample material by small stones, stipes, grains of foreign seed or seeds which are atypically coloured, broken up, germinating or foul.

The chosen seeds (ca. 2 g) were ground in a mixer mill for 5 minutes at 30 Hz. The ground stock was transferred after grinding into a sealable polypropylene container and—if not immediately used for measurement—stored at 4° C. for not more than 96 hours.

150 mg ground stock were mixed with 1.5 ml water and mixed in the mixer mill for 3 minutes at 30 Hz to gain an aqueous extract. 50 µl sodium phosphate buffer and 25 µl NMR standard (consisting of 2 mmol/l trimethylsilyl propionate [TSP] in $D_2O$) were added to 425 µl of this aqueous extract. This mixture was then transferred into a 5-mm NMR sample tube for the subsequent NMR measurement. The measurement was done under the same conditions as the measurement of the coffee extract according to the second exemplary embodiment.

This mustard extraction and NMR measurement was repeated for different kinds or types of mustard seeds. FIG. 18 shows an NMR spectrum of mustard seed extract measured in this way. The spectrum consists of ca. 300 relevant peaks. The intensity on the y-axis is depicted in arbitrary units over the chemical shift in ppm on the x-axis. Signals lying in the range of resonances of water are suppressed.

The measured NMR spectrum was converted into a synthetic spectrum by line separation (cf. for details the according explanations with respect to the second exemplary embodiment).

Figure 19:
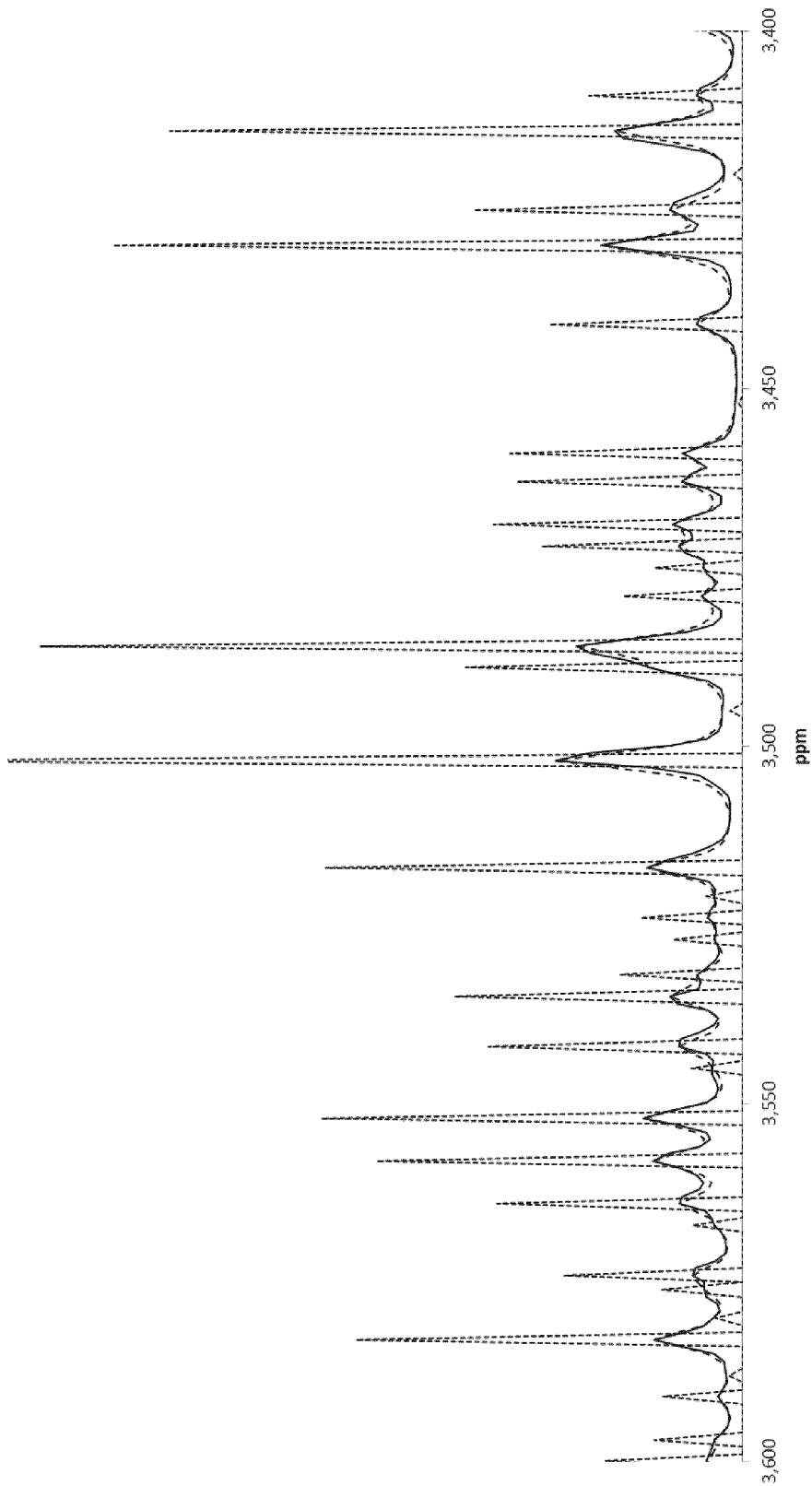
FIG. 19 shows an excerpt of an original NMR spectrum of mustard seed extract together with its synthetic spectrum.

FIG. 19 shows an excerpt of the original spectrum (continuous line) together with its synthetic spectrum (dashed line with broad gaps) and the according integrals of the observed peaks (dashed line with narrow gaps).

180 peaks of the synthetic spectrum were selected and the values of the areas of the according peaks were used to generate a 180×180 correlation matrix. The 32400 values of this matrix are the values of the quotients between two single values of the areas in each case. This correlation matrix can also be referred to as fingerprint matrix.

Different subsequent NMR measurements of different mustard samples of the same mustard variety resulted in a plurality of fingerprint matrices. All of these matrices were summed up to an average correlation matrix for the respective mustard variety. This enhances the reliability of the obtained data.

Afterwards, the whole procedure was repeated for another mustard variety so that two average correlation matrices resulted, one for each variety or group.

Subsequently, all individual correlation matrices were compared to both average correlation matrices by using a delta matrix (weighting matrix) serving as multiplication matrix. The delta matrix was then optimized in such a way that most of the individual correlation matrices showed a small deviation from the average correlation matrix of the same group but a high deviation from the average correlation matrix of the other group.

The according optimization of the delta matrix will be now explained in more detail. This optimization is an iterative process. Initially (first iteration), the delta matrix was filled with the value of 1.0 in all matrix fields. Subsequently, one single value of 1.0 was raised by 10% to the value of 1.1. If the separation between both groups was ameliorated (i.e. deviation of the considered correlation matrix to the average correlation matrix of the same group became smaller and/or the deviation of the considered correlation matrix to the average correlation matrix of the other group became higher), the value of 1.1 was used as starting point for the second iteration. If the separation between both groups became worse, the value of 1.0 was lowered by 10% to 0.9. If the separation now became better, 0.9 was used as starting point for the second iteration. In the second iteration, the respective starting point was again raised and/or lowered by 10% to achieve a better separation of the groups. Factors deviating from 10% can also be used, wherein the factor needs not to be constant during the optimization.

After a plurality of iterations, the optimized value reached either asymptotically the value being best for the separation or asymptotically zero. If it was lower than a pre-determined threshold value, it was set to zero.

This proceeding was then repeated for all other values of the delta matrix. As a result, the delta matrix contained many fields having the value of 0.0 (insignificant correlations) and some fields having higher values (significant correlations). In other words, the delta matrix was simplified to relevant or significant correlations. This weighted delta matrix represents the characterizing signature of the examined system, i.e. of the mustard varieties. Thus, the method of generating a signature provides a simplification of numerous relations between individual signals to only significant relations. In other words, all values being present in the signature are weighted with respect to their significance. The thus simplified delta matrix was then multiplied with the tested correlation matrix. A weighted correlation matrix containing many fields having the value of 0.0 (insignificant correlations) and some fields having high values (significant correlations) resulted.

Subsequently, a variety-specific characterizing signature was generated according to the preceding explanations for all mustard varieties to be examined. Afterwards, a sample of a non-disclosed mustard variety (blind sample) was analyzed in an analogous way. Then, rating values being indicative for the deviation of the signature of the blind sample from each of the signatures of the already examined mustard varieties were calculated. To be more specific, a weighted correlation matrix of the sample to be tested was compared with mean correlation matrices of already analyzed mustard varieties. The weighting was done by using the according optimized delta matrix (i.e. the signature). The individual rating values were calculated analogously to the score value explained above, namely according to the formula:

rating value=(distance $A_i$)/(distance($A$ without $A_i$))

In this case "$A_i$" denotes a first mean correlation matrix of a single mustard variety (i=1 to n) and "A" the sum of the n mean correlation matrices of all n mustard varieties being already analyzed. "A without A" thus denotes the sum of the (n−1) mean correlation matrices of all (n−1) mustard varieties being already analyzed with the exception of mustard variety $A_i$. Thus, a plurality of rating values were calculated (namely n rating values), one for each already existing signature or already analyzed mustard variety, respectively.

Specifically, the signature of the blind sample showed the deviations (expressed as rating value) indicated in the following table 8.

TABLE 8

Rating value of the signature of the blind sample in comparison to the signatures of four mustard varieties.

| Mustard variety | Rating value |
|---|---|
| Sinus | 0.01 |
| Tango | 6.78 |
| Seco | 5.32 |
| Ascot | 13.69 |

The smaller the rating value, the smaller is the deviation of the considered signatures. Thus, the blind sample could be characterized as a sample of the mustard variety "Sinus".

The subsequent tables 9 and 10 represent further experimental data showing the unambiguous identification of the mustard variety of other blind samples.

TABLE 9

Rating value of the signature of the first further blind sample in comparison to the signatures of eleven mustard varieties.

| Mustard variety | Rating value |
|---|---|
| Tango | 0.06 |
| Sirtaki | 2.18 |
| Albatros | 3.47 |
| Seco | 3.61 |
| Litember | 4.36 |
| Radena | 4.48 |
| Semper | 7.14 |
| Bardena | 7.31 |
| Sinus | 9.96 |
| Accent | 10.17 |
| Ascot | 24.66 |

Thus, the first further blind sample could be unambiguously assigned to the mustard variety "Tango".

TABLE 10

Rating value of the signature of the second further blind sample in comparison to the signatures of eleven mustard varieties.

| Mustard variety | Rating value |
|---|---|
| Sinus | 0.16 |
| Ascot | 2.17 |
| Bardena | 3.58 |
| Seco | 3.60 |
| Semper | 4.54 |
| Albatros | 6.74 |
| Radena | 6.92 |
| Litember | 7.61 |
| Accent | 10.28 |
| Sirtaki | 11.86 |
| Tango | 19.60 |

Thus, the second further blind sample could be unambiguously assigned to the mustard variety "Sinus".

By repeating the explained procedure for further blind samples, most of those samples could be correctly assigned to the respective mustard varieties. The sensitivity (true positive rate) was in the range of 91 to 100% for blind samples belonging to one of the eleven mustard varieties indicated above. The samples that could not correctly be assigned to "their" mustard variety showed nonetheless a very low rating value for the correct variety, but an even slightly lower rating value for a false mustard variety.

Within the whole analysis, different batches of the single mustard varieties were examined to assess whether batch-specific differences like cultivation location or cultivation weather are to be considered as having a significant influence on the characterizing signature. It turned out that the characterizing signatures are mainly independent on batch-specific criteria so that a batch-independent identification of different mustard varieties is possible.

Since the signature of each sample to be classified or identified has to be compared with all existing signatures, the accuracy of the method increases with an increasing number of stored signatures.

Now, FIG. 20 will be explained in connection to a forth exemplary embodiment.

Forth Exemplary Embodiment: Monitoring the therapeutic development in the treatment of prostate carcinoma In the therapy of prostate carcinoma, usually super agonists of gonadotropin-releasing hormone like leuprorelin, goserelin or buserelin are used for androgen suppression. These super agonists are applied as implant to suppress testosterone-dependent tumour growth over a longer period of time. The implants are usually designed to release the drug during 1 month.

In this exemplary embodiment, it was examined whether androgen suppressing therapy leads to a significant change in tumour metabolism that can be observed by examining urine samples of patients and analyzing them by NMR techniques using characterizing signatures.

28 Patients suffering from prostate carcinoma and being subjected to a leuprorelin or a goserelin therapy were included in the instant study. The urine of these patients was collected and analyzed by NMR spectroscopy. Sample preparation and NMR measurement was done analogously to the second exemplary embodiment (using 425 µl urine instead of coffee extract).

NMR spectra of urine obtained on day 0 (prior to implanting a leuprorelin or goserelin implant) were analyzed as first group. These NMR spectra represented tumour metabolism without androgen suppression.

NMR spectra of urine obtained on day 28 (on this day the first implant was replaced by a second, fresh implant) were analyzed as second group. These NMR spectra represented tumour metabolism under androgen suppression.

Those lines of the NMR spectra of both groups, on the basis of which a statistically significant distinction between both groups was possible, were separated. In doing so, a weighted correlation matrix (delta matrix) indicating significant correlations between significant lines or peaks was obtained (cf. for the general principle the preceding exemplary embodiments). Instantly, a 61×61 correlation matrix was drawn up.

For validating, urine from men not having a prostate carcinoma was analyzed in an analogous way. The NMR spectra of this third group could be unambiguously differentiated from the NMR spectra of the first and second group. Thus, the characterizing signatures (represented by the respective delta matrix) drawn up for the prostate carcinoma patients (both for group 1 and for group 2) were well suited to differentiate healthy from ill people and were thus obviously based on tumour-specific signals.

Afterwards, causative substances were assigned to the peaks which were identified as significant. This assignment took place by applying three significance groups (assured assignment; probable assignment; possible assignment). The result of the assignment is depicted in the following table 11.

TABLE 11

Assignment of substances to significant peaks.

| Significance | Metabolite | Signal/ppm |
|---|---|---|
| assured | Citrate | 2.669/2.673/2.695/2.699 |
|  | Creatinine | 4.048 |
| highly probable | Malonate | 3.111 |
|  | Methyl malonate | 1.205 |
|  | Methyl guanidine | 2.829 |
|  | Dimethyl succinate | 1.213 |
|  | Hydroxy isovalerate | 1.232 |
|  | Tartrate | 4.347 |
|  | Salicylate | 7.019/7.025/7.489 |
|  | Hypoxanthine | 8.194 |
| possible | Hydroxy butyrate | 1.205 |
|  | Allothreonine | 1.205 |
|  | 1-Methyl urate | 3.259 |
|  | Trimethylamine-N-oxide | 3.259 |
|  | Glycolate | 3.914 |
|  | 5-Hydroxy methyluracil | 4.347 |
|  | 3-Hexene dione acid | 5.698 |

TABLE 11-continued

Assignment of substances to significant peaks.

| Significance | Metabolite | Signal/ppm |
|---|---|---|
|  | Xanthine | 7.935 |
|  | Formiate | 8.371 |
|  | Fatty acid (derivate) | 2.167 |
|  | Histamine | 7.984/7.990/8.000 |
|  | Dimethyl aminopurine | 7.984/7.990/8.000 |
|  | Benzoate | 7.885 |

It is known from prior art that the biosynthesis of fatty acids and phospholipids, the biosynthesis of proteins and amino acids and the biosynthesis of nucleotides is activated in tumour cells. Furthermore, an increased amount of reactive oxygen species, an increased occurrence of toxic metabolites (like non-canonical nucleotides) and the activation of unusual and manifold energy sources can be observed in tumour cells.

In contrast to other tissue, prostate epithelium shows an accumulation of citrate due a limitation of the isocitrate generation. Malignant prostate carcinoma cells loose this capability of citrate accumulation. Whereas the citrate concentration in healthy prostate tissue is ca. 20 000 nmol/g, it is only 500 nmol/g (i.e. less than 2.5%) in malignant tissue.

Since citrate is a central molecule for the overall regulation of metabolism, such a dramatic change in citrate concentration is to be expected to have influence on the biosynthesis of amino acids, proteins and nucleotides. The concentration of citrate and intermediates of the citric acid cycle have a direct influence onto the oxidative phosphorylation and lipid metabolism. The finding that signals caused by citrate play a significant role in the signature characterizing the tumour metabolism appears thus very sensible.

Creatinine is also a characteristic metabolism product that could be unambiguously identified to play an important role for the tumour-metabolism specific signature. Creatinine is the final product of muscular energy metabolism and is excreted as waste product in the urine. Other identified substances are tightly connected to intermediates of the citric acid cycle. Without going into details, the inventors could assign a relevant metabolic role to almost each of the substances listed in table 11. Thus, the composition of the characterizing signature is not arbitrary but indeed reflects the tumour metabolism.

Figure 20:
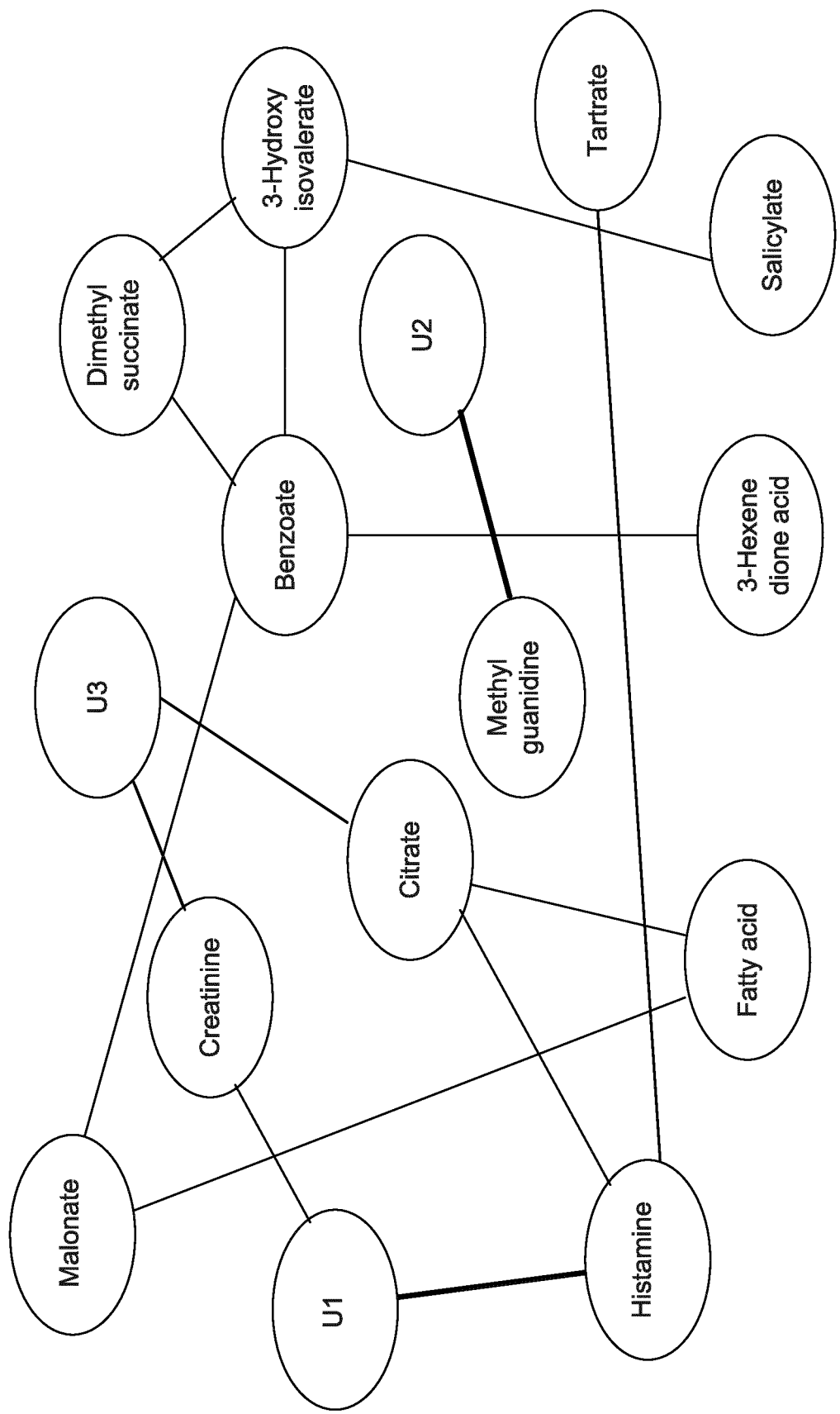
FIG. 20 shows a schematic depiction of a metabolic network for substances playing a role in tumour metabolism.

FIG. 20 represents a network of interrelated substances, the NMR signals of which were considered when generating the characterizing signature. "U1", "U2" and "U3" denote three yet unidentified substances. Some exogenic substances like salicylate and tartrate can be most probably attributed to medication. Although they are not directly connected to tumour metabolism, they could reflect secondary effects due to the available metabolic energy for "normal" metabolic processes.

Subsequently, NMR spectra of urine obtained on day 85 (a third implant was given at day 58) were analyzed as forth group. These NMR spectra also represented tumour metabolism under androgen suppression.

A novel characterizing tumour signature using the NMR spectra of the first group (day 0) and the forth group (day 85) was generated. In doing so, those lines of the NMR spectra of both groups, on the basis of which a statistically significant distinction between both groups was possible, were separated. Then, a weighted correlation matrix (delta matrix) indicating significant correlations between significant lines or peaks was obtained (cf. for the general principle the preceding exemplary embodiments). Instantly, a 61×61 correlation matrix was drawn up.

This second tumour signature showed a high overlap with the first tumour signature (built up on the basis of NMR spectra of the first and second group). E.g., citrate, creatinine, methyl malonate, β-hydroxy isovalerate, xanthine and hypoxanthine could be identified as substances being causative for the lines considered in this novel signature. This underlines the significance of these substances for monitoring changes in tumour metabolism.

The second tumour signature was validated like the first tumour signature, i.e. by comparing it to the signature of men not having a prostate carcinoma. The observed development of the rating values can be used as indication for the progression of anti-tumour therapy: The smaller the deviation between the signature of a tumour patient subjected to therapy and the signature of a person not suffering from a tumour, the better the therapy works. By monitoring the development of the rating values over time, therapy control and assessment can take place.

In summary, it could be proven that androgen suppressing therapy leads to a significant change in tumour metabolism that can be observed by examining urine samples of patients and analyzing them by NMR techniques using characterizing signatures. It could further be established that therapy progression can be effectively monitored by using characterizing signatures.

Figure 21:
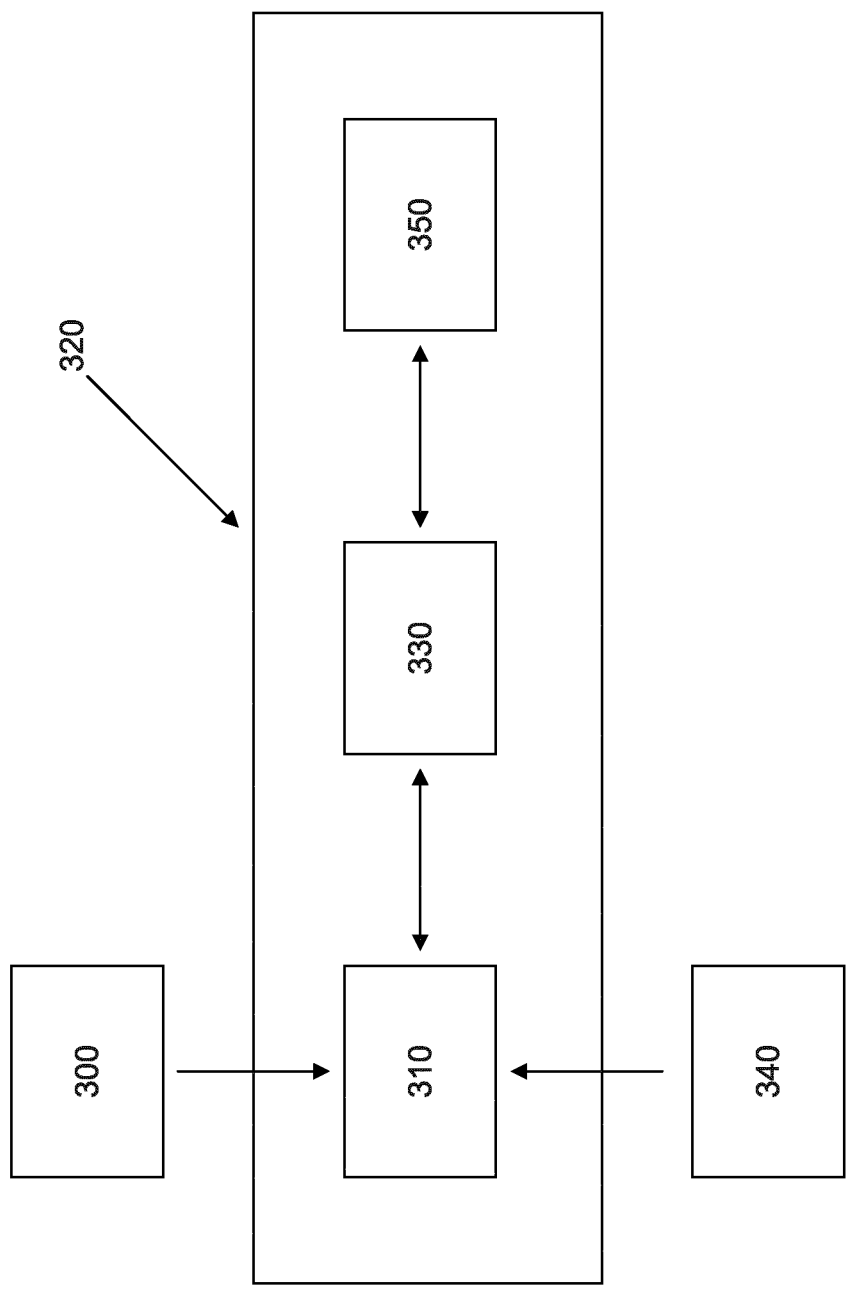
FIG. 21 is a schematic depiction of a computer system.

Turning now to FIG. 21, a schematic depiction of a computer system is illustrated, on which an exemplary software 300 can be executed which is suited for carrying out a method as explained above. This software 300 is loaded into the memory 310 of a computer 320. The processor 330 now executes the software. Subsequently, experimental data 340 in form of a numeric analysis result of a sample are fed into the memory 310 of the computer. The software 300 now chooses (either automatically or by a user input) a subset of numeric values of the experimental data 340. The processor 330 then calculates quotients as mathematic relations between all chosen values, wherein one quotient between two values is calculated at a time. A matrix of $n^2$ values results, wherein n denotes the number of the chosen values.

Afterwards, the significance of the single quotients is determined by the processor 340 while still executing the software 300. Different methods for this purpose have been explained above. This step results in a matrix consisting of many zeros and some values differing from zero. This matrix is the characterizing signature to be generated which is then stored in the memory 310. It is possible to compare this signature with other stored signatures to calculate a distance between the signatures. The result of this comparison can be displayed on a display 350 of the computer 320. This output can, e.g., be information on:
a) the probability that a person will reject a transplanted kidney,
b) the belonging of the sample to a certain coffee variety,
c) the belonging of the sample to a certain mustard variety,
d) the effect of a therapy against a tumour.

Figure 22:
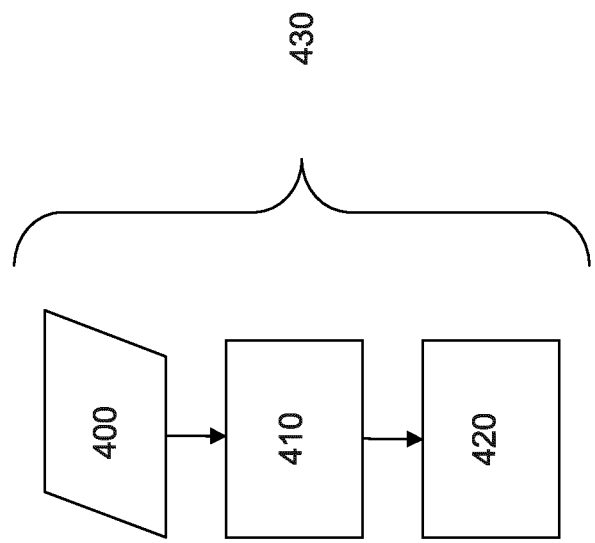

FIG. 22 schematically depicts a flow chart of an embodiment of the method for characterizing a sample explained above. NMR data 400 as analysis result of a sample are provided. A value of a mathematic relation (e.g. a quotient) between at least two values of the NMR data 400 is calculated in step 410. In an embodiment, many values of the mathematic relation are calculated for individual pairs of two values of the NMR data 400 so that a correlation matrix results in step 410. Subsequently, in step 420 a characterizing signature is generated on the basis of the matrix obtained in step 410. This signature can be, e.g., be illustrated as delta matrix. Data 400 and processing steps 410 and 420 can be summarized as method 430.

FIG. 23 schematically depicts a flow chart of an embodiment of the method for characterizing a system explained above. First, in step 500 a sample taken from a system to be characterized is taken. This sample is then analyzed in step 510 by an analysis method like NMR spectroscopy. An analysis result is obtained. This analysis result is used to carry out said method 430 for characterizing a sample (cf. FIG. 22 for details). By this method, a characterizing signature is obtained. In step 520, the obtained signature is compared to a comparative signature. In step 530, a deviation of the signature generated in step 430 and the comparative signature is determined. This deviation can, e.g., be a score or a rating value. In step 540, the deviation is assigned to the system.

The invention claimed is:

1. A method for characterizing a system, comprising the following steps:
providing a first analysis result having a plurality of values, wherein the first analysis result was generated by an analysis of a first sample taken from a system by an analysis method chosen from a group consisting of NMR spectroscopy, mass spectrometry, electron spin resonance, vibrational spectroscopy, UV/VIS spectroscopy, and fluorescence spectroscopy;
determining a first set of values of a quotient between pairs of two values of a first plurality of values;
generating a characterizing signature of a first sample on a basis of the first set of values of the quotient by weighting the first set of values of the quotient with respect to their significance by carrying out the following steps:
a) determining a first deviation between the first set of values of the quotient and a first average correlation matrix that has been obtained by summing up a plurality of a second set of values of a quotient, wherein the second set of values of the quotient has been obtained by providing a second analysis result having a second plurality of values, wherein the second analysis result method is the same analysis used for the first analysis result, and determining the second set of values of a quotient between the first set of values;
b) determining a second deviation between the first set of values of the quotient and a second average correlation matrix that has been obtained by summing up a plurality of a third set of values of a quotient, wherein the third set of values of the quotient has been obtained by providing a third analysis result having a third plurality of values, wherein the third analysis result was generated by an analysis of a sample belonging to a second group by the same analysis method used for the first analysis result, and determining the third set of values of a quotient between a pair of two values of the third plurality of values;
c) providing a weighting set of values having a value of 1.0 each;
d) raising one single value of the weighting set by a factor;
e) multiplying each value of the first set of values of quotients with an according value of the weighting set;

f) determining a first deviation between the first set of values of the quotient and the first average correlation matrix, and determining a second deviation between the first set of values of the quotient and the second average correlation matrix;

g) if the determined first deviation is smaller than in the preceding step and/or if the determined second deviation is bigger than in the preceding step and/or if the determined second deviation is smaller than in the preceding step, lowering the single value of the weighting set again by a factor;

h) repeating steps d) to g) until a modified value reaches asymptotically a value being best for separation, or asymptotically zero;

i) setting the modified value to zero if it is lower than a pre-determined threshold value; and j) repeating steps c) to i) for all other values of the weighting set in order to obtain an optimized weighting set serving as characterizing signature;

multiplying the values of the quotient with the values of the characterizing signature to obtain a weighted set of values being characteristic for the first sample; and using the weighted set of values for characterizing the first sample of the system.

2. The method according to claim 1, wherein the first sample comprises a body fluid of an individual, in particular blood, urine, bile, tissue fluid, sperm, lymph, saliva or cerebrospinal fluid, a culture medium, seeds, a plant extract, or food.

3. The method according to claim 1, wherein the first sample is analyzed with at least two analysis methods.

4. The method according to claim 1, wherein each value of the first, second, and/or third analysis result is correlated with each other value of the same analysis result to obtain a plurality of values of a quotient between two values of the analysis result in each case.

5. The method according to claim 4, wherein a subset is chosen out of the plurality of values of a quotient, said subset being used to generate the signature.

6. The method according to claim 1, wherein the mathematic relation is the ratio of the respective values to each other.

7. The method according to claim 1, wherein the characterizing signature is generated without prior to this assigning substances to the values of the analysis result used for generating the characterizing signature, said substances being causative for these values of the analysis result.

8. The method according to claim 1, wherein characterizing the first sample of the system, comprises using the weighted set of values for one of the following selected from the group consisting of:

determining the health status of the individual by classifying the first sample taken from an individual into one of at least two predefined groups being representative for different health statuses of the individual;

determining the risk of an organ rejection after a transplantation of said organ or determining an organ function for the individual by grouping the first sample taken from an individual into one of at least two predefined groups being representative for different risks of an organ rejection after a transplantation of said organ or for different levels of organ function;

determining a suitability of a plant or seed to be used in a culturing process regarding a production of at least one plant or seed ingredient by grouping the first sample into one of at least two predefined groups being representative for different suitabilities of the plant or the seed to be used in the culturing process regarding the production of the at least one plant or seed ingredient and choosing the plant or seed having the desired suitability for the culturing process for further cultivation steps of the culturing process;

determining the quality of the first sample with respect to at least one of a quantitative and a qualitative determination of the presence of an ingredient in the first sample by grouping the first sample into one of at least two predefined groups being representative for different qualities of the first sample with respect to the ingredient;

determining the origin of an organism by grouping the first sample into one of at least two predefined groups being representative for different origins of the organism; and classifying a biological system or an industrial system representing a biological process into one of different levels of efficiency by grouping the first sample taken from the biological system or the industrial system representing a biological process, into one of at least two predefined groups being representative for different efficiencies of the biological system or the industrial system representing a biological process.

9. The method according to claim 8, wherein the health status indicates an efficacy of a therapy of the individual against a disease.

10. The method according to claim 9, wherein the disease is a tumor-associated disease.

11. The method according to claim 1, wherein characterizing the system indicates a status of a development or a progression of a disease.

12. The method according to claim 9, wherein the disease is a tumor-associated disease.

13. A computer program product for characterizing a system, comprising a non-transitory computer-readable medium having program instructions that, when executed, cause a processor to perform the steps of:

receiving a first analysis result having a plurality of values, wherein the first analysis result was generated by an analysis of a first sample taken from a system by an analysis method chosen from the group consisting of NMR spectroscopy, mass spectrometry, electron spin resonance, vibrational spectroscopy, UV/VIS spectroscopy, and fluorescence spectroscopy;

determining a first set of values of a quotient between pairs of two values of a first plurality of values;

generating a characterizing signature of a first sample on a basis of the first set of values of the quotient by weighting the first set of values of the quotient with respect to their significance by carrying out the following steps:

a) determining a first deviation between the first set of values of the quotient and a first average correlation matrix that has been obtained by summing up a plurality of a second set of values of a quotient, wherein the second set of values of the quotient has been obtained by providing a second analysis result having a second plurality of values, wherein the second analysis result method is the same analysis used for the first analysis result, and determining the second set of values of a quotient between the first set of values;

b) determining a second deviation between the first set of values of the quotient and a second average correlation matrix that has been obtained by summing up a plurality of a third set of values of a quotient, wherein the third set of values of the quotient has been obtained by providing a third analysis result having a third plurality of values, wherein the third analysis result was generated by an analysis of a sample belonging to a second group by the same analysis method used for the first analysis result, and determining the third set of values of a quotient between a pair of two values of the third plurality of values;

c) providing a weighting set of values having a value of 1.0 each;

d) raising one single value of the weighting set by a factor;

e) multiplying each value of the first set of values of quotients with an according value of the weighting set;

f) determining a first deviation between the first set of values of the quotient and the first average correlation matrix, and determining a second deviation between the first set of values of the quotient and the second average correlation matrix;

g) if the determined first deviation is smaller than in the preceding step and/or if the determined second deviation is bigger than in the preceding step and/or if the determined second deviation is smaller than in the preceding step, lowering the single value of the weighting set again by a factor;

h) repeating steps d) to g) until a modified value reaches asymptotically a value being best for separation, or asymptotically zero;

i) setting the modified value to zero if it is lower than a pre-determined threshold value; and j) repeating steps c) to i) for all other values of the weighting set in order to obtain an optimized weighting set serving as characterizing signature;

multiplying the values of the quotient with the values of the characterizing signature to obtain a weighted set of values being characteristic for the first sample; and using the weighted set of values for characterizing the first sample of the system.

\* \* \* \* \*

UNITED STATES PATENT AND TRADEMARK OFFICE
CERTIFICATE OF CORRECTION

Page 1 of 1

PATENT NO. : 10,497,465 B2
APPLICATION NO. : 13/878094
DATED : December 3, 2019
INVENTOR(S) : Fritz Huber et al.

It is certified that error appears in the above-identified patent and that said Letters Patent is hereby corrected as shown below:

In the Claims

Column 32, Line 33, Claim 12, delete "claim 9," and insert -- claim 11, --

Signed and Sealed this
Third Day of March, 2020

Andrei Iancu
*Director of the United States Patent and Trademark Office*